US012171802B2

(12) United States Patent
Medved et al.

(10) Patent No.: US 12,171,802 B2
(45) Date of Patent: Dec. 24, 2024

(54) COMPOSITIONS FOR INHIBITING FIBRIN-VLDL RECEPTOR-DEPENDENT INFLAMMATION AND METHODS OF TREATMENT

(71) Applicants: Leonid V. Medved, Ellicott City, MD (US); Dudley Strickland, Brookeville, MD (US); Sergiy Yakovlev, Rockville, MD (US)

(72) Inventors: Leonid V. Medved, Ellicott City, MD (US); Dudley Strickland, Brookeville, MD (US); Sergiy Yakovlev, Rockville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/306,824

(22) PCT Filed: Jun. 2, 2017

(86) PCT No.: PCT/US2017/035654
§ 371 (c)(1),
(2) Date: Dec. 3, 2018

(87) PCT Pub. No.: WO2017/210539
PCT Pub. Date: Dec. 7, 2017

(65) Prior Publication Data
US 2019/0151415 A1    May 23, 2019

Related U.S. Application Data

(60) Provisional application No. 62/344,531, filed on Jun. 2, 2016.

(51) Int. Cl.
| A61K 39/00 | (2006.01) |
| A61K 38/17 | (2006.01) |
| A61K 38/36 | (2006.01) |
| A61K 39/395 | (2006.01) |
| A61P 9/10 | (2006.01) |
| A61P 37/06 | (2006.01) |
| C07K 16/28 | (2006.01) |

(52) U.S. Cl.
CPC ........ *A61K 38/1774* (2013.01); *A61K 38/363* (2013.01); *A61P 9/10* (2018.01); *A61P 37/06* (2018.01); *C07K 16/28* (2013.01); *A61K 2039/505* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,271,144 | B2 | 9/2007 | Petzelbauer | |
| 8,722,623 | B2* | 5/2014 | Medved | C07K 14/75 |
| | | | | 514/13.6 |
| 2006/0263360 | A1 | 11/2006 | Goldstein | |
| 2007/0048383 | A1 | 3/2007 | Helmus | |
| 2008/0004220 | A1 | 1/2008 | Petzelbauer | |
| 2012/0289467 | A1* | 11/2012 | Medved | C07K 14/75 |
| | | | | 514/13.6 |

FOREIGN PATENT DOCUMENTS

| WO | 2007095659 A1 | 8/2007 |
| WO | 2007095660 A1 | 8/2007 |

OTHER PUBLICATIONS

Perman et al.The VLDL receptor promotes lipotoxicity and increases mortality in mice following an acute myocardial infarction. J Clin Invest. 2011;121(7):2625-2640 (Year: 2011).*
Ruiz et al. The apoE isoform binding properties of the VLDL receptor reveal marked differences from LRP and the LDL receptor. J Lipid Res. 2005;46(8):1721-1731. (Year: 2005).*
Owens RJ, Young RJ. The genetic engineering of monoclonal antibodies. J Immunol Methods. 168(2): 149-165, 1994. (Year: 1994).*
Yakovlev et al. Interaction of fibrin with VE-cadherin and anti-inflammatory effect of fibrin-derived fragments. Journal of Thrombosis and Haemostasis, 9: 1847-1855 (Year: 2011).*
Petzelbauer P, Zacharowski PA, Miyazaki Y, et al. The fibrin-derived peptide B β(15-42) protects the myocardium against ischemia-reperfusion injury. Nat Med. 2005;11(3):298-304. (Year: 2005).*
Perman et al. Mechanisms of Acute Ischemia-Dependent Myocardial Lipid Accumulation: A Novel Role for the Very-Low-Density-Lipoprotein Receptor. Conference: 77th Congress of the European Atherosclerosis Society (EAS 2008), Istanbul (Turkey), Apr. 26, 2008—29 A (Year: 2008).*
Yakovlev et al. Identification of VLDLR as a novel endothelial cell receptor for fibrin that modulates fibrin-dependent transendothelial migration of leukocytes. Blood. 2012; 119(2):637-644. (Year: 2012).*
Yang et al. SaIA Attenuates Ischemia/Reperfusion Induced Endothelial Barrier Dysfunction via Down-Regulation of VLDL Receptor Expression. Cell Physiol Biochem 2014;33:747-757. (Year: 2014).*
Petzelbauer et al., The fibrin-derived peptide Bβ15-42 protects the myocardium against ischemia-reperfusion Injury, Nature Medicine, (2005), 11: 298-304.
Roesner et al., The fibrin-derived peptide Bβ15-42 is cardioprotective in a pig model of myocardial ischemia-reperfusion injury, Crit Care Med, (2007), 35: 1730-1735.

(Continued)

*Primary Examiner* — Maher M Haddad
(74) *Attorney, Agent, or Firm* — Nevrivy Patent Law Group P.L.L.C.

(57) ABSTRACT

The invention provides a method of treating inflammation, comprising administering to a subject in need thereof a therapeutically effective amount of an agent that inhibits binding of fibrin to Very Low Density Lipoprotein Receptor (VLDLR) or combination of this agent with agents inhibiting binding of fibrin to VE-cahherin (vascular endothelial cadherin).

25 Claims, 7 Drawing Sheets

Specification includes a Sequence Listing.

(56) References Cited

OTHER PUBLICATIONS

Zacharowski et al., The Effects of the Fibrin-derived Peptide Bβ15-42 in Acute and Chronic Rodent Models of Myocardial Ischemia-Reperfusion, Shock, (2007), 27: 631-637.
Wadia et al., Protein transduction technology, Current Opinion in Biotechnology (2002), 13:52-56.
Jones et al., Characterisation of cell-penetrating peptide-mediated peptide delivery, British Journal of Pharmacology, (2005), 145:1093-1102.
Schlesinger et al., Growth-modulating serum tripeptide is glycyl-histidyl-lysine, Cellular and Molecular Life Sci, (1977), 33: 324-325.
Zheng, Photocrosslinked Peg Hydrogel and Peptide Flourescent Sensors for Copper Ions, Dissertation, Univeristy of Miami, (2002), p. 1-3.
Gorlatov et al., Interaction of Fibrin (ogen) with the Endothelial Cell Receptor VE-Cadherin: Mappling of the Receptor-Bindin Site in the NH2-Terminal Portions of the Fibrin β Chains, Biochemistry, (2002), 41: 4107-4116.
Roberts et al., Chemistry for peptide and protein PeGylation, Advanced Drug Delivery Reviews, (2002), 54:459-476.
Masson-Bessie're et al., The Major Synovial Targets of the Rheumatoid Arthritis-Specific Antifilaggrin Autoantibodies are Deiminated Forms of the α- and β-Chains of Fibrin the Journal of Immunology, (2001), 166:4177-4184.
Carden et al., Pathophysiology of ischaemia±reperfusion injury, J Pathol, (2000), 190:255±266.
Yakovlev et al., Anti-VLDL receptor monoclonal antibodies inhibit fibrin-VLDL receptor interaction and reduce fibrin-dependent leukocyte transmigration, Thromb Haemost, (2016), 116(6):1122-1130.
Strickland et al., Identification of a Monoclonal Antibody Specific for a Neoantigenic Determinant on α2-Macroglobulin: Use for the Purification and Characterization of Binary Proteinase-Inhibitor Complexes, Biochemistry, (1988), 27:1458-1466.
Ashcom et al., The Human α-Macroglobulin Receptor: Identification of A 420-KD Cell Surface Glycoprotein Specific for the Activated Conformation of α2-Macroglobulin, The Journal of Cell Biology, (1990), 110:1041-1048.

\* cited by examiner

SEQUENCE LISTING

```
<160> NUMBER OF SEQ ID NOS: 17

<210> SEQ ID NO 1
<211> LENGTH: 24
<212> TYPE: PRT
<213> ORGANISM: Artificial sequence
<220> FEATURE:
<223> OTHER INFORMATION: synthetic peptide

<400> SEQUENCE: 1

Gly His Arg Pro Leu Asp Lys Arg Glu Ala Pro Ser Leu Arg Pro Ala
1               5                   10                  15

Pro Ile Ser Gly Tyr Arg Cys Gly
            20

<210> SEQ ID NO 2
<211> LENGTH: 26
<212> TYPE: PRT
<213> ORGANISM: Artificial sequence
<220> FEATURE:
<223> OTHER INFORMATION: synthetic peptide

<400> SEQUENCE: 2

Gly His Arg Pro Leu Asp Lys Lys Arg Glu Glu Ala Pro Ser Leu Arg
1               5                   10                  15

Pro Ala Pro Pro Pro Ile Ser Tyr Cys Gly
            20                  25

<210> SEQ ID NO 3
<211> LENGTH: 21
<212> TYPE: PRT
<213> ORGANISM: Artificial sequence
<220> FEATURE:
<223> OTHER INFORMATION: synthetic peptide

<400> SEQUENCE: 3

Gly His Arg Pro Leu Asp Lys Lys Arg Glu Glu Ala Pro Ser Leu Arg
1               5                   10                  15

Pro Ala Tyr Cys Gly
            20

<210> SEQ ID NO 4
<211> LENGTH: 19
<212> TYPE: PRT
<213> ORGANISM: Artificial sequence
<220> FEATURE:
<223> OTHER INFORMATION: synthetic peptide

<400> SEQUENCE: 4

Gly His Arg Pro Leu Asp Lys Lys Arg Glu Glu Ala Pro Ser Leu Arg
1               5                   10                  15

Tyr Cys Gly
```

```
<210> SEQ ID NO 5
<211> LENGTH: 18
<212> TYPE: PRT
<213> ORGANISM: Artificial sequence
<220> FEATURE:
<223> OTHER INFORMATION: synthetic peptide

<400> SEQUENCE: 5

Gly His Arg Pro Leu Asp Lys Lys Arg Glu Glu Ala Pro Ser Leu Arg
1               5                   10                  15

Cys Gly

<210> SEQ ID NO 6
<211> LENGTH: 52
<212> TYPE: PRT
<213> ORGANISM: Artificial sequence
<220> FEATURE:
<223> OTHER INFORMATION: synthetic peptide

<400> SEQUENCE: 6

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

Gly Gly Cys Gly
        50

<210> SEQ ID NO 7
<211> LENGTH: 51
<212> TYPE: PRT
<213> ORGANISM: Artificial sequence
<220> FEATURE:
<223> OTHER INFORMATION: synthetic peptide

<400> SEQUENCE: 7

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

Gly Gly Cys
        50

<210> SEQ ID NO 8
<211> LENGTH: 6
<212> TYPE: PRT
<213> ORGANISM: Artificial sequence
<220> FEATURE:
<223> OTHER INFORMATION: synthetic peptide

<400> SEQUENCE: 8

Leu Lys Lys Thr Glu Thr
1               5

<210> SEQ ID NO 9
<211> LENGTH: 6
<212> TYPE: PRT
<213> ORGANISM: Artificial sequence
<220> FEATURE:
<223> OTHER INFORMATION: synthetic peptide
```

<400> SEQUENCE: 9

Leu Lys Lys Thr Asn Thr
1               5

<210> SEQ ID NO 10
<211> LENGTH: 7
<212> TYPE: PRT
<213> ORGANISM: Artificial sequence
<220> FEATURE:
<223> OTHER INFORMATION: synthetic peptide

<400> SEQUENCE: 10

Lys Leu Lys Lys Thr Glu Thr
1               5

<210> SEQ ID NO 11
<211> LENGTH: 7
<212> TYPE: PRT
<213> ORGANISM: Artificial sequence
<220> FEATURE:
<223> OTHER INFORMATION: synthetic peptide

<400> SEQUENCE: 11

Leu Lys Lys Thr Glu Thr Gln
1               5

<210> SEQ ID NO 12
<211> LENGTH: 34
<212> TYPE: DNA
<213> ORGANISM: Artificial sequence
<220> FEATURE:
<223> OTHER INFORMATION: primer

<400> SEQUENCE: 12
gatcgccaac atatgccaac ctgtggcgcc catg                           34

<210> SEQ ID NO 13
<211> LENGTH: 52
<212> TYPE: DNA
<213> ORGANISM: Artificial sequence
<220> FEATURE:
<223> OTHER INFORMATION: primer

<400> SEQUENCE: 13
gctgctcgag tcagtggtgg tggtggtggt gagagggaca gttgacctca tc       52

<210> SEQ ID NO 14
<211> LENGTH: 33
<212> TYPE: DNA
<213> ORGANISM: Artificial sequence
<220> FEATURE:
<223> OTHER INFORMATION: primer

<400> SEQUENCE: 14
gatcgccaac atatgcgaac ttgccgacct gac                            33

<210> SEQ ID NO 15
<211> LENGTH: 52
<212> TYPE: DNA
<213> ORGANISM: Artificial sequence
<220> FEATURE:
<223> OTHER INFORMATION: primer

<400> SEQUENCE: 15
gctgctcgag tcagtggtgg tggtggtggt gacactcttt cagggctca tc        52

<210> SEQ ID NO 16
<211> LENGTH: 66
<212> TYPE: PRT
<213> ORGANISM: Artificial sequence
<220> FEATURE:
<223> OTHER INFORMATION: synthetic peptide

<400> SEQUENCE: 16

```
Gln Gly Val Asn Asp Asn Glu Glu Gly Phe Phe Ser Ala Arg Gly His
1               5                   10                  15

Arg Pro Leu Asp Lys Lys Arg Glu Glu Ala Pro Ser Leu Arg Pro Ala
            20                  25                  30

Pro Pro Pro Ile Ser Gly Gly Gly Tyr Arg Ala Arg Pro Ala Lys Ala
        35                  40                  45

Ala Ala Thr Gln Lys Lys Val Glu Arg Lys Ala Pro Asp Ala Gly Gly
    50                  55                  60

Cys Gly
65
```

<210> SEQ ID NO 17
<211> LENGTH: 1473
<212> TYPE: DNA
<213> ORGANISM: Homo sapiens

<400> SEQUENCE: 17

| | | | | | |
|---|---|---|---|---|---|
| atgaaaagga | tggtttcttg | gagcttccac | aaacttaaaa | ccatgaaaca | tctattattg | 60 |
| ctactattgt | gtgtttttct | agttaagtcc | caaggtgtca | acgacaatga | ggagggtttc | 120 |
| ttcagtgccc | gtggtcatcg | acccctttgac | aagaagagag | aagaggctcc | cagcctgagg | 180 |
| cctgccccac | cgcccatcag | tggaggtggc | tatcgggctc | gtccagccaa | agcagctgcc | 240 |
| actcaaaaga | agtagaaag | aaaagcccct | gatgctggag | gctgtcttca | cgctgaccca | 300 |
| gacctggggg | tgttgtgtcc | tacaggatgt | cagttgcaag | aggctttgct | acaacaggaa | 360 |
| aggccaatca | gaaatagtgt | tgatgagtta | ataacaatg | tggaagctgt | tcccagacc | 420 |
| tcctcttctt | cctttcagta | catgtatttg | ctgaaagacc | tgtggcaaaa | gaggcagaag | 480 |
| caagtaaaag | ataatgaaaa | tgtagtcaat | gagtactcct | cagaactgga | aaagcaccaa | 540 |
| ttatatatag | atgagactgt | gaatagcaat | atcccaacta | accttcgtgt | gcttcgttca | 600 |
| atcctggaaa | acctgagaag | caaaatacaa | agttagaat | ctgatgtctc | agctcaaatg | 660 |
| gaatattgtc | gcaccccatg | cactgtcagt | tgcaatattc | ctgtggtgtc | tggcaaagaa | 720 |
| tgtgaggaaa | ttatcaggaa | aggaggtgaa | acatctgaaa | tgtatctcat | tcaacctgac | 780 |
| agttctgtca | aaccgtatag | agtatactgt | gacatgaata | cagaaaatgg | aggatggaca | 840 |
| gtgattcaga | accgtcaaga | cggtagtgtt | gactttggca | ggaaatggga | tccatataaa | 900 |
| cagggatttg | gaaatgttgc | aaccaacaca | gatgggaaga | attactgtgg | cctaccaggt | 960 |
| gaatattggc | ttgaaatga | taaaattagc | cagcttacca | ggatgggacc | cacagaactt | 1020 |
| ttgatagaaa | tggaggactg | gaaaggagac | aaagtaaagg | ctcactatgg | aggattcact | 1080 |
| gtacagaatg | aagccaacaa | ataccagatc | tcagtgaaca | aatacagagg | aacagccggt | 1140 |
| aatgccctca | tggatggagc | atctcagctg | atgggagaaa | acaggaccat | gaccattcac | 1200 |
| aacggcatgt | tcttcagcac | gtatgacaga | gacaatgacg | gctggttaac | atcagatccc | 1260 |
| agaaaacagt | gttctaaaga | agacggtggt | ggatggtggt | ataatagatg | tcatgcagcc | 1320 |
| aatccaaacg | gcagatacta | ctggggtgga | cagtacacct | gggacatggc | aaagcatggc | 1380 |

```
acagatgatg gtgtagtatg gatgaattgg aagggtcat ggtactcaat gaggaagatg    1440
agtatgaaga tcaggccctt cttcccacag caa                                1473
```

COMPOSITIONS FOR INHIBITING FIBRIN-VLDL RECEPTOR-DEPENDENT INFLAMMATION AND METHODS OF TREATMENT

CROSS-REFERENCE TO RELATED APPLICATIONS

This application claims the benefit of U.S. Provisional Appl. No. 62/344,531, filed Jun. 2, 2016, the contents of which are hereby incorporated by reference in their entirety.

Incorporation-By-Reference of Material Submitted Electronically Incorporated by reference in its entirety herein is a computer-readable sequence listing submitted concurrently herewith and identified as follows: One 7016 Byte ASCII (Text) file named "Sequence_Listing_ST25.txt," created on Jun. 1, 2017.

STATEMENT OF FEDERALLY SPONSORED RESEARCH AND DEVELOPMENT

This invention was made with government support under Grant Numbers HL056051 and HL120388, awarded by the National Institutes of Health. The government has certain rights in the invention.

FIELD OF THE INVENTION

The field of the invention generally relates to the fields of medicine, molecular biology and anti-inflammatory therapeutics.

BACKGROUND

Fibrinogen is the major plasma protein involved in hemostasis and other important physiological and pathological processes. Activation of the blood coagulation cascade upon vascular injury results in generation of thrombin, which converts soluble fibrinogen into an insoluble polymeric fibrin. Fibrin polymer serves as the basis for blood clots that seal the injured vasculature to prevent blood loss and as a provisional matrix that participates in subsequent wound healing process (Clark RA., Ann NY Acad Sci 2001; 936: 355-367), which includes inflammation, tissue formation, angiogenesis, etc. Fibrin(ogen) has been implicated in inflammation. It has been proposed that fibrinogen or fibrin degradation products promote transendothelial migration of leukocytes and thereby inflammation through their interaction with endothelial receptors ICAM-1 or VE-cadherin, respectively (Altieri D C., Thromb Haemost 1999; 82: 781-786; Petzelbauer P, et al., Nat Med 2005; 11: 298-304). It has also been found that fibrin promotes leukocyte transmigration through its interaction with another endothelial cell receptor, the very low density lipoprotein (VLDL) receptor (Yakovlev S, et al., Blood 2012; 119: 637-644).

Fibrinogen is a chemical dimer consisting of two identical subunits, each of which includes three non-identical polypeptide chains, Aa, Bβ, and γ (Henschen A, McDonagh J., Zwaal R F A, Hemker H C, eds. Amsterdam, Elsevier Science Publishers 1986; pp 171-241; Medved L, Weisel J W, J Thromb Haemost 2009; 7: 355-359). The central region of the fibrinogen molecule is formed by N-terminal portions of all 6 chains linked together by 11 disulfide bonds, and is often called the N-terminal disulfide knot (NDSK) (Blomback B, et al., Nature 1968; 218: 130-134). Upon conversion of fibrinogen into fibrin, thrombin removes from this region, namely from the N-terminal portions of the Aa and Bβ chains, fibrinopeptides A and B (FpA and FpB), respectively (Medved L, Weisel J W, J Thromb Haemost 2009; 7: 355-359). Digestion of fibrinogen with CNBr results in an NDSK fragment corresponding to fibrinogen central region. Treatment of NDSK with thrombin converts it into NDSK-II lacking FpA and FpB. Such fragment corresponds to the central region of fibrin. NDSK-II retains some binding sites of fibrin and is often used as a simple fibrin mimetic in functional studies. Specifically, it has been shown that this fragment interacts with endothelial VE-cadherin (Bach T L, et al., J Biol Chem 1998; 273: 30719-30728) and this interaction promotes angiogenesis (Martinez J, et al. Ann N Y Acad Sci 2001; 936: 386-405) and inflammation (Petzelbauer P, et al., Nat Med 2005; 11: 298-304). The VE-cadherin-binding site has been localized to a pair of fibrin βN-domains formed by the β chain residues 15-64 present in the NDSK-II fragment (Gorlatov S, Medved L., Biochemistry 2002; 41: 4107-4116). It was also demonstrated that the recombinant (β15-66)$_2$ fragment, mimicking the dimeric arrangement of these domains in fibrin, interacts with VE-cadherin with practically the same affinity as fibrin (Gorlatov S, Medved L., Biochemistry 2002; 41: 4107-4116). Furthermore, it has been found that fibrin interacts with the VLDL receptor through its βN-domains and (β15-66)$_2$ corresponding to these domains has practically the same affinity to VLDLR as fibrin (Yakovlev S, et al., Blood 2012; 119: 637-644). Thus, the (β15-66)$_2$ fragment retains functional properties of fibrin βN-domains.

The VLDL receptor (VLDLR) is a member of the low density lipoprotein receptor family. It functions as a peripheral lipoprotein receptor involved in the delivery of triglyceride-rich lipoproteins to peripheral tissue (Takahashi S, et al., Proc Natl Acad Sci USA 1992; 89: 9252-9256; Sakai J, et al., J Biol Chem 1994; 269: 2173-2182) and also plays an important role in reelin signaling (Trommsdorff M, et al., Cell 1999; 97: 689-701; Herz J, Chen Y., Nat Rev Neurosci 2006; 7: 850-859), angiogenesis and tumor growth (Hembrough T A, et al., Blood 2004; 103: 3374-3380), and fibrin-dependent inflammation (Yakovlev S, et al., Blood 2012; 119: 637-644). VLDLR consists of one polypeptide chain that forms the extracellular portion, the transmembrane domain, and the cytoplasmic domain (Takahashi S, et al., J Atheroscler Thromb 2004; 11: 200-208; Lillis A P, et al., Physiol Rev 2008; 88: 887-918). The extracellular portion, which includes 8 complement-type repeats (CR-domains), and EGF-like, (3-propeller, and the 0-linked sugar domains, has been expressed in the insect expression system (Ruiz J, et al., J Lipid Res 2005; 46: 1721-1731). The ligand-binding region of VLDLR including all 8 CR-domains has been expressed in the bacterial expression system and used in functional studies, as well as an antigen for preparation of anti-VLDLR monoclonal antibodies (Ruiz J, et al., J Lipid Res 2005; 46: 1721-1731). Three such antibodies, 1H10, 1H5, and 5F3, have been prepared and partially characterized (Ruiz J, et al., J Lipid Res 2005; 46: 1721-1731). However, the exact location of their epitopes has not been established.

This background information is provided for informational purposes only. No admission is necessarily intended, nor should it be construed, that any of the preceding information constitutes prior art against the present invention

SUMMARY

It is to be understood that both the foregoing general description of the embodiments and the following detailed description are exemplary, and thus do not restrict the scope of the embodiments.

It is shown herein that interaction of three anti-VLDLR monoclonal antibodies, mAb 1H10, 1H5, and 5F3, with recombinant fragments of VLDLR containing various combinations of its CR-domains were tested and it was determined that the epitopes for mAb 1H10 and mAb 1H5 overlap with the fibrin-binding site of VLDLR. Based on these findings, mAb 1H10 and mAb 1H5 inhibition of fibrin-VLDLR interactions and modulation of leukocyte transmigration was assessed. The data herein demonstrates that these monoclonal antibodies both have high affinity to the fibrin-binding fragments of the VLDL receptor and efficiently inhibit interaction between the VLDLR-binding fragment of fibrin and the fibrin-binding fragments of VLDLR. Further, in in vitro experiments using a leukocyte transendothelial migration assay, it is shown herein that both monoclonal antibodies efficiently inhibit leukocyte transmigration induced by fibrin mimetic NDSK-II. Further, in vivo experiments using a mouse model of peritonitis shown herein reveal that mAb 1H10 and mAb 1H5 both significantly reduce infiltration of leukocytes into the peritoneum. Furthermore, experiments using a mouse model of myocardial ischemia-reperfusion injury shown herein reveal that both monoclonal antibodies significantly reduce myocardial injury induced by ischemia-reperfusion. Thus, the results shown herein indicate that monoclonal antibodies 1H10 and 1H5 are novel specific inhibitors of a fibrin-VLDLR-dependent leukocyte transmigration pathway. They can be used for treatment of fibrin-dependent inflammation including myocardial ischemia-reperfusion injury.

In one aspect, the invention provides a method of treating inflammation, comprising administering to a subject in need thereof a therapeutically effective amount of an agent that inhibits binding of fibrin to Very Low Density Lipoprotein Receptor (VLDLR). In some embodiments, the agent is an antibody that is selected from antibody 1H10 or 1H5. In some embodiments, the method treats myocardial injury induced by ischemia and reperfusion in the subject. In some aspects, the method further comprises administering to the subject an agent that inhibits binding of fibrin to VE-cadherin.

In another aspect, the invention provides a composition comprising a therapeutic agent that inhibits binding of fibrin to Very Low Density Lipoprotein Receptor (VLDLR) and a therapeutic agent that inhibits binding of fibrin to VE-cadherin. In some embodiments, the agent that inhibits binding of fibrin to Very Low Density Lipoprotein Receptor (VLDLR) is an antibody such as antibody 1H10 and/or 1H5. In some embodiments, the therapeutic agent that inhibits binding of fibrin to VE-cadherin is a peptide comprising an amino acid sequence of a fibrin beta chain fragment of a Bbeta chain of fibrinogen or a derivative thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

Figure 1:
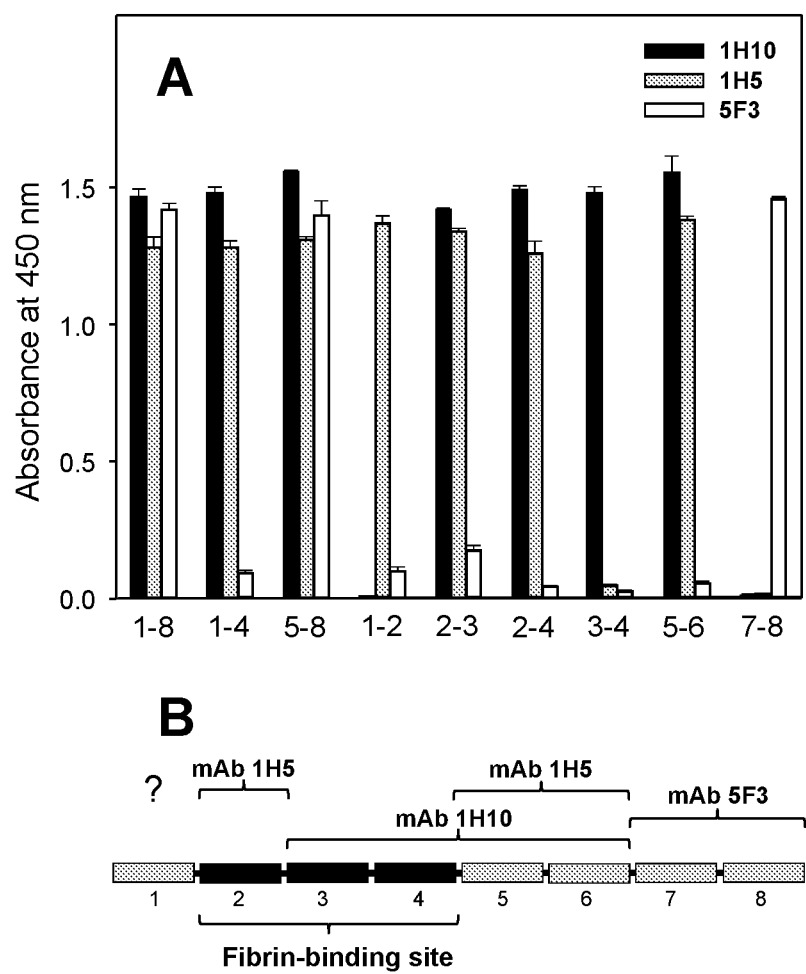
FIG. 1. Localization of the epitopes for the anti-VLDLR monoclonal antibodies used herein. A) ELISA-detected interaction between the anti-VLDLR monoclonal antibodies, 1H10 (black bars), 1H5 (grey bars), and 5F3 (empty bars), and various VLDLR fragments. The three monoclonal antibodies, each at 1 μg/mL, were incubated with microtiter wells coated with the recombinant VLDLR(1-8), VLDLR (1-4), VLDLR(5-8), VLDLR(1-2), VLDLR(2-3), VLDLR (2-4), VLDLR(3-4), VLDLR(5-6), and VLDLR(7-8) fragments, and the bound mAbs were detected with the goat anti-mouse secondary antibodies as described in Materials and methods. The corresponding VLDLR fragments are indicated by numbers (1-8, 1-4, 5-8, etc.). The bars are representative of at least 2 independent experiments; error bars represent the standard deviation of triplicate determinations. B) Schematic representation of the ligand-binding region of the VLDL receptor including 8 CR-domains; the previously localized fibrin-binding CR-domains 2-4 (Yakovlev S, Medved L. Interaction of Fibrin with the Very Low Density Lipoprotein Receptor: Further Characterization and Localization of the Fibrin-Binding Site. Biochemistry 2015; 54: 4751-4761) are presented by black bars; the epitopes localized for each of the 3 mAb are indicated.

The invention is based on the discovery of therapeutic agents that can block fibrin binding to VLDLR and treat, suppress or prevent inflammation.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of." The term "about" as used herein refers to an amount that is within 10% of the numerical value recited.

In one embodiment, the invention provides a method of treating inflammation, comprising administering to a subject in need thereof a therapeutically effective amount of an agent that inhibits binding of fibrin to Very Low Density Lipoprotein Receptor (VLDLR).

In some embodiments, the therapeutically effective amount of an agent that inhibits binding of fibrin to Very Low Density Lipoprotein Receptor (VLDLR) is an antibody. The term "antibody" is used to refer to any antibody like molecule that has an antigen binding region, and includes full length antibody molecules, antibody fragments such as Fab', Fab, F(ab')2, single domain antibodies (DABs), Fv, scFv (single chain Fv), and the like. The techniques for preparing and using various antibody based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (mAbs) as used herein also include sequences corresponding to human antibodies, animal antibodies, and combinations thereof. The term "chimeric antibody," as used herein, includes antibodies that have variable regions derived from an animal antibody, such as a rat or mouse antibody, fused to another molecule, for example, the constant domains derived from a human antibody. One type of chimeric antibodies, "humanized antibodies," have had the variable regions altered (through mutagenesis or CDR grafting) to match (as much as possible) the known sequence of human variable regions. CDR grafting involves grafting the CDRs from an antibody with desired specificity onto the FRs of a human antibody, thereby replacing much of the non-human sequence with human sequence. Humanized antibodies, therefore, more closely match (in amino acid sequence) the sequence of known human antibodies. By humanizing mouse monoclonal antibodies, the severity of the human anti-mouse antibody, or HAMA, response is diminished.

In some embodiments, the antibody can bind at least one complement-type repeat (CR) domain of VLDLR selected from the group consisting of CR-2, CR-3 and CR-4, or any combination thereof. In some embodiments, the antibody can bind to CR domains 3-6. In some embodiments, the antibody can bind to CR domains 1-2 and 5-6. In some embodiments, the antibody can bind to CR domains 2 and 5-6.

In some embodiments, the antibody is a monoclonal antibody. In some embodiments, the antibody is a mouse monoclonal antibody. In some embodiments, the antibody is 1H10. In some embodiments, the antibody is 1H5. In some embodiments, the antibody comprises one or more complementarity determining regions (CDRs) identical to the CDRs of 1H10 or 1H5. Antibodies 1H10 and 1H5 are available commercially from Molecular Innovations (Novi, MI).

In some embodiments, it may be desirable to "humanize" the antibody in order to attenuate any adverse immune reaction. Humanized antibodies can be produced, for example by replacing an immunogenic portion of an antibody with a corresponding, but non-immunogenic portion (i.e., chimeric antibodies). See, e.g., Robinson et al., WO/1987/002671; Akira et al., EP Application 184,187; Taniguchi, EP Application 171,496; Morrison et al., EP Application 173,494; Neuberger et al., WO 86/01533; Cabilly et al., EP Application 125,023, all of which are incorporated herein by reference. In some embodiments, the agent that inhibits binding of fibrin to Very Low Density Lipoprotein Receptor (VLDLR) is a humanized antibody. In some embodiments, the antibody is a humanized antibody of antibody 1H10 or 1H5. In some embodiments, the antibody is a fully human antibody.

As used herein, a "therapeutically effective amount" is an amount of an agent or composition that alleviates, totally or partially, the pathophysiological effects of inflammation, ischemia and reperfusion, or other pathological indication of the invention. Unless otherwise indicated, the agent or composition is administered at a concentration that is a therapeutically effective amount. A therapeutically effective amount can also be an amount that is given prophylactically thereby inhibiting any pathophysiological effects of inflammation, ischemia and reperfusion, or other pathological indication of the invention. A therapeutically effective amount will depend upon, for example, subject size, gender, magnitude of the associated disease, condition, or injury, and genetic or non-genetic factors associated with individual pharmacokinetic or pharmacodynamic properties of the administered agent or composition. For a given subject in need thereof a therapeutically effective amount can be determined by one of ordinary skill in the art.

As used herein, "treat" and all its forms and tenses (including, for example, treat, treating, treated, and treatment) refer to both therapeutic treatment and prophylactic or preventative treatment. A subject in need of treatment includes those already with a pathological condition of the invention as well as those in which a pathological condition of the invention is to be prevented.

The terms "inhibiting," "reducing," or "prevention," or any variation of these terms, when used in the claims and/or the specification includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The subject to be administered the therapeutic agent is not limiting. In some embodiments, the subject is a mammal including for example, a dog, cat, monkey, goat, pig, chimpanzee, cow, horse, sheep, rabbit, guinea pig, rat, hamster, mouse, and human. In some embodiments, the subject is a human.

In some embodiments, the invention provides a method of treating a pathophysiological effect of inflammation, ischemia and reperfusion, myocardial ischemia and reperfusion, or other pathological indication. In some embodiments, the invention provides a method of treating a pathophysiological effect of inflammation, ischemia and reperfusion, myocardial ischemia and reperfusion, or other pathological indication wherein such is present as an acute condition as opposed to a long-term or chronic condition. In some embodiments, the invention provides a method of treating, inhibiting, reducing or at least partly preventing inflammation in a subject and/or promoting tissue protection and/or regeneration by contacting the tissue with an effective amount of a therapeutic agent as described herein. In some embodiments, the tissue comprises coronary tissue of the subject.

In some embodiments, the methods comprise administering the therapeutic agent to a subject suffering from or at risk of myocardial infarction (commonly referred to as a heart attack or cardiac tissue damage as a result of hypoxia), stroke, and other types of organ or tissue ischemia and reperfusion (including, for example, hepatic ischemia and reperfusion, renal ischemia and reperfusion, intestinal ischemia and reperfusion, or other gastrointestinal ischemia and reperfusion, neuronal ischemia and reperfusion, ischemic neuropathies, surgical-induced ischemia and reperfusion, ischemia and reperfusion associated with organ transplantation, preservation of an ischemic and reperfused organ for organ transplantation, etc.). In some embodiments, the invention encompasses treating a subject suspected of undergoing ischemia and reperfusion, a subject susceptible of undergoing ischemia and reperfusion, or a subject known to be undergoing ischemia and reperfusion. For example, if a subject is presented at an emergency room or other healthcare setting with symptoms of a heart attack (including, for example, chest pain, shortness of breath, etc.) the invention encompasses treating such subject by administering the therapeutic agent disclosed herein. The invention also encompasses treating a subject that is going under programmed or planned ischemia and reperfusion (including, for example, cardiac bypass surgery, angioplasty, other cardiovascular surgeries or procedures implicating ischemia and reperfusion, etc.) by administering the therapeutic agent disclosed herein.

In some embodiments of the invention, the administration of the therapeutic agent inhibits transendothelial migration of leukocytes in the subject. In some embodiments, the administration of the therapeutic agent inhibits transendothelial migration of leukocytes in the subject by about 10%, 20%, 30%, 40%, 50%, 60%, 70%, 80%, 90% or more in the subject. In some embodiments, the administration of the therapeutic agent reduces the infiltration of leukocytes into the peritoneum of the subject. In some embodiments, the administration of the therapeutic agent reduces the infiltration of leukocytes into the peritoneum of the subject by about 10%, 20%, 30%, 40%, 50%, 60%, 70%, 80%, 90% or more.

In one embodiment, the invention provides a method for treating or reducing reperfusion injury caused by myocardial infarction in a subject by administering to the subject an effective amount of a therapeutic agent as described herein. In some embodiments, the method is performed between 1 minute and 720 minutes after the beginning or the ending of a myocardial infarction. In some embodiments, the method is performed between 1 minute and 360 minutes after the beginning or the ending of a myocardial infarction. In some embodiments, the method is performed between 1 minute and 180 minutes after the beginning or the ending of a myocardial infarction. In some embodiments, the method is performed between 1 minute and 60 minutes after the beginning or the ending of a myocardial infarction. In some embodiments, the method is performed between 1 minute and 30 minutes after the beginning or the ending of a myocardial infarction.

The therapeutic agents described herein can be administered in any effective amount. For example, therapeutic agents such as antibodies or peptides can be administered in dosages of each within the range of about 0.0001-1,000,000 micrograms, in amounts within the range of about 0.1-100,000 micrograms, in amounts within the range of about 1-10,000 micrograms, in amounts within the range of about 1-5,000 micrograms, and in amounts within the range of about 1-1000 micrograms. Such dosages can be measured in a µg/kg or mg/kg basis.

Therapeutic agents can be administered daily, every other day, every other week, every other month, etc., with a single application or multiple applications per day of administration, such as administrations of 2, 3, 4 or more times per day.

In some embodiments, the therapeutic agent is injected right before reperfusion to reduce reperfusion injury. In some embodiments, one or more additional injections after reperfusion, e.g., within a few hours, is performed to maintain an appropriate level of the therapeutic in the circulation.
Combination Therapies In another embodiment, the therapeutic methods as described herein comprise administering to the subject a therapeutically effective amount of an agent that inhibits binding of fibrin to Very Low Density Lipoprotein Receptor (VLDLR) in combination with one or more additional therapeutic agents. In some embodiments, the additional therapeutic agent comprises a therapeutically effective amount of an agent that inhibits binding of fibrin to VE-cadherin. In some embodiments, the therapeutic agent that inhibits binding of fibrin to VE-cadherin comprises a fibrin beta chain fragment of a Bbeta chain of fibrinogen or a derivative thereof. Suitable fibrin beta chain fragments of a Bbeta chain of fibrinogen are disclosed in U.S. Pat. No. 8,722,623, which is incorporated by reference herein.

Figure 7:
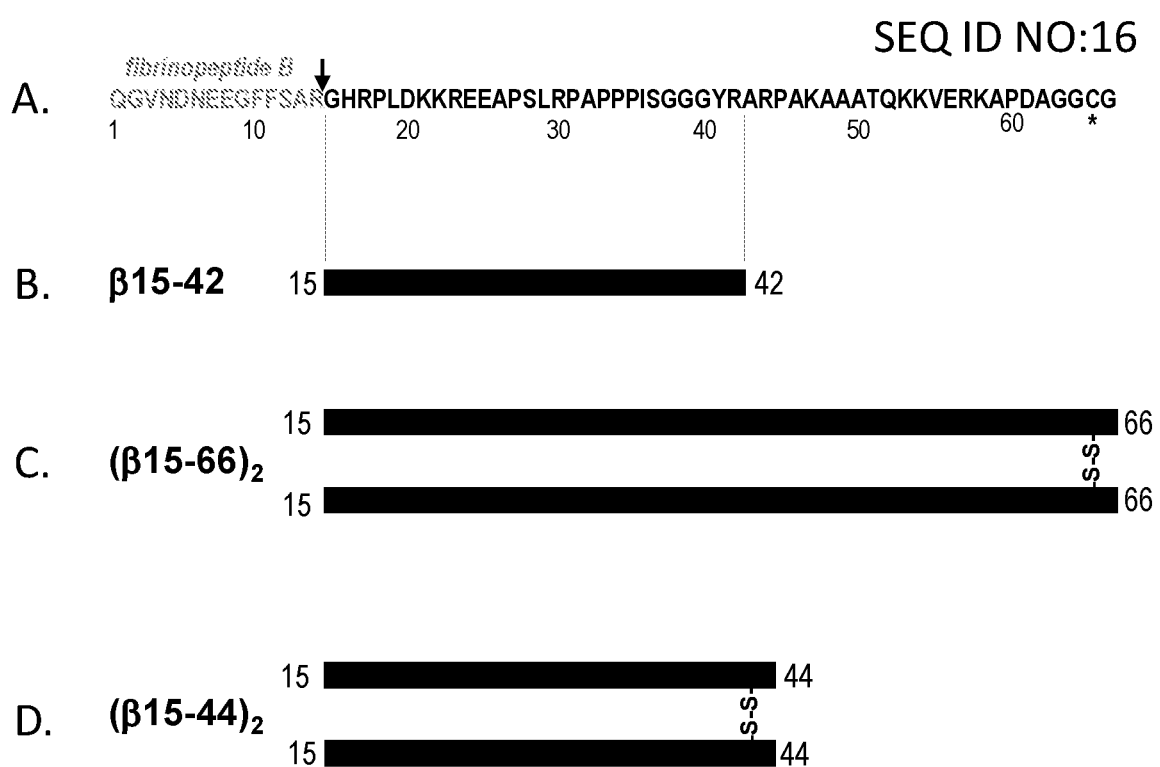
FIG. 7. (A) shows the amino acid sequence of fibrinogen Bbeta chain (SEQ ID NO:16) including fibrinopeptide B and fibrin beta chain fragment. (B) is a schematic representation of a monomeric β15-42 fragment of the sequence shown in (A). (C) is a schematic representation of a dimeric (β15-66)$_2$ peptide. (D) schematically represents a (β15-44)$_2$ peptide.

As used herein, a "fibrin beta chain fragment of a Bbeta chain of fibrinogen" or derivative thereof means a peptide derived from the Bbeta chain of fibrinogen (see, for example, Petzelbauer et al. Nat Med. 2005 Mar; 11(3):298-304. Epub 2005 Feb. 20; Gorlatov et al. Biochemistry (2002) 41, 4107-4116; U.S. Pat. No. 4,980,456; GENE BANK ACCESSION NO. NP 005132). In some embodiments, such peptides can be in the form of a monomer or dimer. If the peptide is not indicated to be in the monomeric or dimeric form, the peptide encompasses both the monomeric and dimeric form. FIG. 7A shows the amino acid sequence of fibrinogen Bbeta chain including fibrinopeptide B and fibrin beta chain fragment. The nucleotide sequence of the Bbeta chain of fibrinogen is shown in SEQ ID NO:17

In some embodiments, the therapeutic agent that inhibits binding of fibrin to VE-cadherin is a peptide of the formula (βX1-X2, wherein said peptide sequence corresponds in whole or in part to an amino acid sequence of a fibrin beta chain fragment of a Bbeta chain of fibrinogen, wherein X1 represents an N-terminal end of said peptide sequence and X2 represents a C-terminal end of said peptide sequence, wherein said peptide sequence includes additional amino acids between X1 and X2, wherein said peptide sequence can contain a non-naturally occurring amino acid residue. In some embodiments, said peptide sequence is other than a wild-type β15-42 monomer sequence. In some embodiments, said peptide sequence is other than (β15-66)$_2$ dimer having two chains with each chain consisting of wild type amino acids (β15-65 and with each chain including a non-naturally occurring Gly at position 66 of each chain.

In some embodiments, the therapeutic agent that inhibits binding of fibrin to VE-cadherin is a synthetic peptide dimer comprising two peptide sequences, each of said sequences comprising amino acids 15-42 of a fibrin beta chain (e.g., amino acids (β15-42 of SEQ ID NO:16) or a VE-cadherin-binding conservative variant thereof, each of said sequences being linked at C-terminal ends thereof. In some embodiments, the dimer has fewer than 104 amino acid residues in total. In another embodiment, the fibrin beta chain or a VE-cadherin-binding conservative variant thereof comprises amino acids 15-32 of SEQ ID NO:16.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

In some embodiments, the therapeutic agent that inhibits binding of fibrin to VE-cadherin is a synthetic peptide comprising an amino acid sequence selected from the group consisting of any of SEQ ID NOS: 1-7.

In some embodiments, the therapeutic agent that inhibits binding of fibrin to VE-cadherin peptide is conjugated to, fused with, or combined with a protein transduction domain (PTD). PTD and methods of protein transduction are set forth in U.S. Pat. No. 8,722,623, which are incorporated by reference herein in their entirety.

In some embodiments, the therapeutic agent is a recombinant dimer β(15-66)$_2$, in which two β15-66 peptides are disulfide-linked via Cys65. In some embodiments, the monomer β(15-66) sequence is SEQ ID NO:6. In some embodiments, the fibrinogen Bbeta chain amino acid sequence (amino acids 1-66) is SEQ ID NO:16.

In some embodiments, the method further comprises administering to the subject a therapeutic agent that inhibits binding of fibrin to VE-cadherin as described herein and a polypeptide agent comprising or consisting essentially of at least one of thymosin β4 (TB4), an isoform of TB4, an N-terminal variant of TB4, a C-terminal variant of TB4, LKKTET (SEQ ID NO:8) or a conservative variant thereof, LKKTNT (SEQ ID NO:9) or a conservative variant thereof, KLKKTET (SEQ ID NO:10) or a conservative variant thereof, LKKTETQ (SEQ ID NO:11) or a conservative variant thereof, TB4 sulfoxide, Tb4$^{ala}$, Tb9, Tb10, Tb 11, Tb12, Tb13, Tb14, Tb15, gelsolin, vitamin D binding protein (DBP), profilin, cofilin, adsevertin, propomyosin, fincilin, depactin, Dnasel, vilin, fragmin, severin, capping protein, b-actinin, acumentin or conservative variants of any of the above. Such polypeptide agents can promote tissue protection and/or regeneration.

In some embodiments, the method comprises administering to a subject in need thereof a therapeutically effective amount of an agent that inhibits binding of fibrin to Very Low Density Lipoprotein Receptor (VLDLR), such as antibody 1H10 or 1H5, in combination with an effective amount of thymosin β4 (TB4) or a biologically active fragment or conservative variant thereof.

In some embodiments, the synthetic peptide dimer comprises two peptide sequences, each of the sequences comprising amino acids 15-42 of a fibrin beta chain (e.g., corresponding to amino acids 15-42 of SEQ ID NO:16), each of the sequences being linked at C-terminal ends thereof. In some embodiments, the dimer has fewer than 104 amino acid residues in total. In some embodiments, the dimer may further comprise at least one additional amino acid residue, or more than one additional amino acid residues. For example, each peptide chain of the dimer may include additional amino acid residues between amino acids 42 and 66 of the fibrin beta chain. For example, the invention may utilize the (1315-66)$_2$ dimer shown in FIG. 7C, or conservative variants thereof.

In some embodiments, the dimer comprises the (β15-44)$_2$ dimer shown in FIG. 7D, or conservative variants thereof. In some embodiments, (β15-44)$_2$ comprises a dimeric version of β15-42 fragment in which two identical β15-42 peptides are disulfide-linked through artificially added Cys43. In some embodiments, the method encompasses using monoclonal antibody mAb 1H5 or mAb 1H10 (or humanized versions thereof or antibodies comprising the CDRs thereof) in combination with the dimeric fibrin-derived (β15-44)$_2$ fragment as an anti-inflammatory agent for treatment of myocardial ischemia reperfusion injury as well as other types of ischemia-reperfusion injuries.

The therapeutic agents as described herein can be administered separately or together. In some embodiments, the therapeutic agents are administered in the same composition. In some embodiments, the therapeutic agents are administered in separate compositions.

In one embodiment, the method comprises administering to the subject a peptide dimer as described herein having fewer than 104 amino acid residues in total, or administering a peptide dimer which further comprises at least one additional amino acid residue. Non-limiting examples include the $(15\text{-}44)_2$ dimer and the $(\beta15\text{-}66)_2$ dimer. In some embodiments, the tissue to be treated is muscle tissue, particularly cardiac tissue.

In some embodiments, the dimer has 60 amino acid residues in total, e.g., the $(\beta15\text{-}44)_2$ dimer. There are 30 amino acid residues in each of two polypeptide chains of the $(\beta15\text{-}44)_2$ peptide; the first 28 residues of each chain correspond to the natural $\beta15\text{-}42$ sequence of human fibrin, while the last two residues, Cys43 and Gly44, are added to link two polypeptide chains together through a Cys43-Cys43 disulfide bond.

In some embodiments, the dimer has 104 amino acid residues in total, e.g., the $(\beta15\text{-}66)_2$ dimer. There are 52 amino acid residues in each of two polypeptide chains of the $(\beta15\text{-}66)_2$ peptide; the first 51 residues including Cys65 of each chain correspond to the natural $\beta15\text{-}65$ sequence of human fibrin, while the last residue, Gly66, can be added to facilitate formation of a Cys65-Cys66 disulfide bond.

In some embodiments, the therapeutic agent that inhibits binding of fibrin to VE-cadherin can also include a dimer including one or more naturally occurring or substituted amino acid residues between residues 42 and 66 of the fibrin beta chain. The two peptide sequences of the dimer can be the same length, or different lengths. One or more amino acids may be substituted for the naturally occurring amino acids of the fibrin beta chain, so long as the dimer retains VE-cadherin binding affinity.

The dimers can be manufactured using solid phase peptide synthesis or recombinant manufacturing methods known in the art.

It is noted that the dimeric form of a fibrin beta chain derived peptide is represented, for example, using the following formula: $(\beta X1\text{-}X2)_2$ wherein "X1" and "X2" indicate an amino position of the Bbeta chain of fibrinogen with or without any additional non-naturally occurring amino acid residues and "2" following the parenthesis indicates that the fibrin beta chain derived peptide exists as a dimer. In certain embodiments described herein, a fibrin beta chain derived peptide in dimeric form has an additional non-naturally occurring amino acid(s) at the C-terminus of the peptide. In other certain embodiments described herein, a fibrin beta chain derived peptide in dimeric form has an additional non-naturally occurring amino acid(s) at the N-terminus end of the peptide.

A fibrin beta chain derived peptide can include both the isolated monomeric form and dimeric form. Such sequences include, for example, those consisting of or comprising the isolated wild-type sequence $\beta15\text{-}32$, $\beta15\text{-}33$, $\beta15\text{-}34$, $\beta15\text{-}35$, $\beta15\text{-}36$, $\beta15\text{-}37$, $\beta15\text{-}38$, $\beta15\text{-}39$, $\beta15\text{-}40$, $\beta15\text{-}41$, $\beta15\text{-}42$, $\beta15\text{-}43$, $\beta15\text{-}44$, $\beta15\text{-}45$, $\beta15\text{-}46$, $\beta15\text{-}47$, $\beta15\text{-}48$, $\beta15\text{-}49$, $\beta15\text{-}50$, $\beta15\text{-}51$, $\beta15\text{-}52$, $\beta15\text{-}53$, $\beta15\text{-}54$, $\beta15\text{-}55$, $\beta15\text{-}56$, $\beta15\text{-}57$, $\beta15\text{-}58$, $\beta15\text{-}59$, $\beta15\text{-}60$, $\beta15\text{-}61$, $\beta15\text{-}62$, $\beta15\text{-}63$, $\beta15\text{-}64$, $\beta15\text{-}65$, $\beta15\text{-}66$, $\beta15\text{-}67$, $\beta15\text{-}68$, $\beta15\text{-}69$, $\beta15\text{-}70$, $\beta15\text{-}71$, $\beta15\text{-}72$, and $\beta15\text{-}73$. Homodimers of these peptides can be formed by, for example, modifying the isolated peptide by engineering a Cys (or a Gly in the case of, for example, $\beta15\text{-}65$) at the end of the sequence, a Cys and a Gly at the end of the sequence, a Tyr, a Cys, and a Gly at the end of the sequence, or other means for producing a homodimeric form of these peptides (see, for example, U.S. Patent Application Publication Nos. 20070225221 20070142295, 20070093418, 20070049532, 20060122370, 20060002931, 20050152896, and 20020051785; U.S. Pat. Nos. 5,767,078 and 7,011,834). In some embodiments (and for illustrative purposes), a dimer consisting of or comprising $(\beta15\text{-}66)_2$ has a non-naturally occurring Gly at position 66 (i.e., amino acid 15-65 correspond to the native protein), $(\beta15\text{-}44)2$ has a non-naturally occurring Cys at position 43 and Gly at position 44 (i.e., amino acid 15-42 correspond to the native protein), $((\beta15\text{-}40)_2$ has a non-naturally occurring Tyr at position 38, Cys at position 39, and Gly at position 40 (i.e., amino acid 15-37 correspond to the native protein), $(\beta15\text{-}39)_2$ has a non-naturally occurring Cys at position 38, and Gly at position 39 (i.e., amino acid 15-37 correspond to the native protein), $(\beta15\text{-}35)_2$ has a non-naturally occurring Tyr at position 33, Cys at position 34, and Gly at position 35 (i.e., amino acid 15-32 correspond to the native protein), $(\beta15\text{-}34)_2$ has a non-naturally occurring Cys at position 33, and Gly at position 34 (i.e., amino acid 15-32 correspond to the native protein), $(\beta15\text{-}33)_2$ has a non-naturally occurring Tyr at position 31, Cys at position 32, and Gly at position 33 (i.e., amino acid 15-30 correspond to the native protein), $(\beta15\text{-}32)_2$ has a non-naturally occurring Cys at position 31, and Gly at position 32 (i.e., amino acid 15-30 correspond to the native protein). In some embodiments, the method not only encompasses monomers described herein as homodimers, but also any combination of heterodimers.

In even further additional embodiments, residues of the native sequence (including, for example, residues 18 and 20) can be mutated by replacing the wild-type amino acid with another natural or non-natural occurring amino acid (see, for example, U.S. Pat. No. 6,783,946). Naturally occurring amino acids include, for example, alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), and valine (V). In some embodiments, substitutions are conservative substitutions. In other embodiments, the substitutions are non-conservative substitutions. In some embodiments, position 18 is mutated from a P to an A and/or position 20 is mutated from a D to an N (see, for example, Gorlatov S., Medved L., Biochemistry (2002; 41: 4107-4116).

Conservative and non-conservative amino acid substitutions are known to those of ordinary skill in the art, for example, substituting an acidic amino acid for another acid amino acid may be considered a conservative substitution whereas substituting a basic amino acid for an acidic amino acid may be considered a non-conservative substitution; similarly, substituting a polar amino acid for another polar acid may be considered a conservative substitution whereas substituting a nonpolar amino acid for a polar amino acid may be considered a non-conservative substitution. Amino acids are generally grouped into the following categories (which can be used as a guide for determining whether or not a substitution is conservative or non-conservative): (1) polar/hydrophilic: S, T, C, N, and Q; (2) non-polar/hydrophobic: G, A, P, V, L, I, and M; (3) acidic: D and E; (4) basic: K, R, and H; and (5) aromatic: F, W, and Y.

Pharmaceutical Compositions

In one embodiment, the invention provides a pharmaceutical composition comprising a therapeutically effective amount of an agent that inhibits binding of fibrin to Very Low Density Lipoprotein Receptor (VLDLR) as described herein.

In some embodiments, the composition further comprises a therapeutically effective amount of thymosin β4 (TB4) or a biologically active fragment or conservative variant thereof.

In some embodiments, the composition further comprises a therapeutically effective amount of an agent that inhibits binding of fibrin to VE-cadherin.

In some embodiments, the therapeutically effective amount of an agent that inhibits binding of fibrin to Very Low Density Lipoprotein Receptor (VLDLR) is an antibody as described herein, such as antibody 1H10 or 1H5 or humanized versions thereof. In some embodiments, the therapeutically effective amount of an agent that inhibits binding of fibrin to VE-cadherin comprises a fibrin beta chain fragment of a Bbeta chain of fibrinogen or a derivative thereof as described herein.

In some embodiments, pharmaceutical compositions of the present invention comprise an effective amount of one or more antibodies, fibrin beta chain fragments of a Bbeta chain of fibrinogen or a derivative thereof, and/or additional agents dissolved or dispersed in a pharmaceutically acceptable carrier. Aqueous compositions of the present invention can comprise an effective amount of therapeutic agents dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

The compositions disclosed herein may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, by inhalation (e.g., aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The pharmaceutical compositions can include one or more solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The use of such media and agents for pharmaceutical active agents is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

In some embodiments, one or more of the therapeutic agents of the invention can be provided in a modified or derivative form (including, for example, polyethylene glycol (PEG) modification or derivatization). WO 92/16221 describes peptides that are covalently linked to long-chain polymers of PEG. The binding of a peptide to such polymers frequently results in a prolongation of the biological half-life of these peptides and delays their metabolism and excretion. A summary of these properties is described by, for example, Davis et al. (Polymeric Materials Pharmaceuticals for Biomedical Use (1980), pp. 441-451). The addition of a PEG-group exerts an increase in biological half-life in a way proportional to the molecular weight of the PEGylated peptide (up to a certain size), as a result of, for example, glomular filtration rate being inversely proportional to molecular weight (see also, for example, U.S. Pat. No. 7,273,909, which describes pegylation of polypeptides and other biomolecules; U.S. Patent Application Publication No. 20050107297, which describes PEG-modified compounds and their use, in particular with emphasis on modified peptides activating the erythropoietin receptor; further examples describing covalent modification of peptides and proteins with PEG residues are interleukins (Knauf et al., J. Biol Chem. 1988, 263, 15064; Tsutumi et al., J. Controlled Release 1995, 33, 447), interferons (Kita et al., Drug Delivery Res. 1990, 6 157), and catalase (Abuchowski et al., J. Biol. Chem. 1997, 252, 3582).

In some embodiments, the PEG can have a molecular weight of about, for example, between 0.5 Kd and 100 Kd, this molecular weight being the minimum and maximum of a molecular weight distribution, so that individual components of the mixture may have a higher or lower molecular weight. In some embodiments, PEG has a molecular weight of about 5 Kd to 50 Kd. In other embodiments, PEG has a molecular weight of about 5 Kd to 30 Kd. In some embodiments, PEG has a molecular weight of about 5 Kd to 10 Kd. In some embodiments, PEG has a molecular weight of about 0.5 Kd, 0.6 Kd, 0.7 Kd, 0.8 Kd, 0.9 Kd, 1 Kd, 1.1 Kd, 1.2 Kd, 1.3 Kd, 1.4 Kd, 1.5 Kd, 1.6 Kd, 1.7 Kd, 1.8 Kd, 1.9 Kd, 2 Kd, 2.1 Kd, 2.2 Kd, 2.3 Kd, 2.4 Kd, 2.5 Kd, 2.6 Kd, 2.7 Kd, 2.8 Kd, 2.9 Kd, 3 Kd, 3.1 Kd, 3.2 Kd, 3.3 Kd, 3.4 Kd, 3.5 Kd, 3.6 Kd, 3.7 Kd, 3.8 Kd, 3.9 Kd, 4 Kd, 4.1 Kd, 4.2 Kd, 4.3 Kd, 4.4 Kd, 4.5 Kd, 4.6 Kd, 4.7 Kd, 4.8 Kd, 4.9 Kd, 5 Kd, 5.1 Kd, 5.2 Kd, 5.3 Kd, 5.4 Kd, 5.5 Kd, 5.6 Kd, 5.7 Kd, 5.8 Kd, 5.9 Kd, 6 Kd, 6.1 Kd, 6.2 Kd, 6.3 Kd, 6.4 Kd, 6.5 Kd, 6.6 Kd, 6.7 Kd, 6.8 Kd, 6.9 Kd, 7 Kd, 7.1 Kd, 7.2 Kd, 7.3 Kd, 7.4 Kd, 7.5 Kd, 7.6 Kd, 7.7 Kd, 7.8 Kd, 7.9 Kd, 8 Kd, 8.1 Kd, 8.2 Kd, 8.3 Kd, 8.4 Kd, 8.5 Kd, 8.6 Kd, 8.7 Kd, 8.8 Kd, 8.9 Kd, 9 Kd, 9.1 Kd, 9.2 Kd, 9.3 Kd, 9.4 Kd, 9.5 Kd, 9.6 Kd, 9.7 Kd, 9.8 Kd, 9.9 Kd, 10 Kd, 10.25 Kd, 10.5 Kd, 10.75 Kd, 11 Kd, 11.25 Kd, 11.5 Kd, 11.75 Kd, 12 Kd, 12.25 Kd, 12.5 Kd, 12.75 Kd, 13 Kd, 13.25 Kd, 13.5 Kd, 13.75 Kd, 14 Kd, 14.25 Kd, 14.5 Kd, 14.75 Kd, 15 Kd, 15.25 Kd, 15.5 Kd, 15.75 Kd, 16 Kd, 16.25 Kd, 16.5 Kd, 16.75 Kd, 17 Kd, 17.25 Kd, 17.5 Kd, 17.75 Kd, 18 Kd, 18.25 Kd, 18.5 Kd, 18.75 Kd, 19 Kd, 19.25 Kd, 19.5 Kd, 19.75 Kd, 20 Kd, 20.25 Kd, 20.5 Kd, 20.75 Kd, 21 Kd, 21.25 Kd, 21.5 Kd, 21.75 Kd, 22 Kd, 22.25 Kd, 22.5 Kd, 22.75 Kd, 23 Kd, 23.25 Kd, 23.5 Kd, 23.75 Kd, 24 Kd, 24.25 Kd, 24.5 Kd, 24.75 Kd, 25 Kd, 25.25 Kd, 25.5 Kd, 25.75 Kd, 26 Kd, 26.25 Kd, 26.5 Kd, 26.75 Kd, 27 Kd, 27.25 Kd, 27.5 Kd, 27.75 Kd, 28 Kd, 28.25 Kd, 28.5 Kd, 28.75 Kd, 29 Kd, 29.25 Kd, 29.5 Kd, 29.75 Kd, 30 Kd, 30.25 Kd, 30.5 Kd, 30.75 Kd, 31 Kd, 31.25

Kd, 31.5 Kd, 31.75 Kd, 32 Kd, 32.25 Kd, 32.5 Kd, 32.75 Kd, 33 Kd, 33.25 Kd, 33.5 Kd, 33.75 Kd, 34 Kd, 34.25 Kd, 34.5 Kd, 34.75 Kd, 35 Kd, 35.25 Kd, 35.5 Kd, 35.75 Kd, 36 Kd, 36.25 Kd, 36.5 Kd, 36.75 Kd, 37 Kd, 37.25 Kd, 37.5 Kd, 37.75 Kd, 38 Kd, 38.25 Kd, 38.5 Kd, 38.75 Kd, 39 Kd, 39.25 Kd, 39.5 Kd, 39.75 Kd, 40 Kd, 40.25 Kd, 40.5 Kd, 40.75 Kd, 41 Kd, 41.25 Kd, 41.5 Kd, 41.75 Kd, 42 Kd, 42.25 Kd, 42.5 Kd, 42.75 Kd, 43 Kd, 43.25 Kd, 43.5 Kd, 43.75 Kd, 44 Kd, 44.25 Kd, 44.5 Kd, 44.75 Kd, 45 Kd, 45.25 Kd, 45.5 Kd, 45.75 Kd, 46 Kd, 46.25 Kd, 46.5 Kd, 46.75 Kd, 47 Kd, 47.25 Kd, 47.5 Kd, 47.75 Kd, 48 Kd, 48.25 Kd, 48.5 Kd, 48.75 Kd, 49 Kd, 49.25 Kd, 49.5 Kd, 49.75 Kd, 50 Kd, 50.5 Kd, 51 Kd, 51.5 Kd, 52 Kd, 52.5 Kd, 53 Kd, 53.5 Kd, 54 Kd, 54.5 Kd, 55 Kd, 55.5 Kd, 56 Kd, 56.5 Kd, 57 Kd, 57.5 Kd, 58 Kd, 58.5 Kd, 59 Kd, 59.5 Kd, 60 Kd, 60.5 Kd, 61 Kd, 61.5 Kd, 62 Kd, 62.5 Kd, 63 Kd, 63.5 Kd, 64 Kd, 64.5 Kd, 65 Kd, 65.5 Kd, 66 Kd, 66.5 Kd, 67 Kd, 67.5 Kd, 68 Kd, 68.5 Kd, 69 Kd, 69.5 Kd, 70 Kd, 70.5 Kd, 71 Kd, 71.5 Kd, 72 Kd, 72.5 Kd, 73 Kd, 73.5 Kd, 74 Kd, 74.5 Kd, 75 Kd, 75.5 Kd, 76 Kd, 76.5 Kd, 77 Kd, 77.5 Kd, 78 Kd, 78.5 Kd, 79 Kd, 79.5 Kd, 80 Kd, 80.5 Kd, 81 Kd, 81.5 Kd, 82 Kd, 82.5 Kd, 83 Kd, 83.5 Kd, 84 Kd, 84.5 Kd, 85 Kd, 85.5 Kd, 86 Kd, 86.5 Kd, 87 Kd, 87.5 Kd, 88 Kd, 88.5 Kd, 89 Kd, 89.5 Kd, 90 Kd, 90.5 Kd, 91 Kd, 91.5 Kd, 92 Kd, 92.5 Kd, 93 Kd, 93.5 Kd, 94 Kd, 94.5 Kd, 95 Kd, 95.5 Kd, 96 Kd, 96.5 Kd, 97 Kd, 97.5 Kd, 98 Kd, 98.5 Kd, 99 Kd, 99.5 Kd, or 100 Kd.

The therapeutic agents disclosed herein can be extensively dialyzed to remove undesired small molecular weight molecules and/or lyophilized for more ready formulation into a desired vehicle, where appropriate. In some embodiments, the therapeutic agents will then generally be formulated for parenteral administration, e.g., formulated for injection via the intravenous, intramuscular, sub-cutaneous, intranasal, intralesional, or even intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It should be stable under the conditions of manufacture and storage and can be preserved against the contaminating action of microorganisms, such as bacteria and fungi.

Solutions of the therapeutic agents as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The therapeutic agents of the present invention can be formulated into a composition in a free base, in a neutral or salt form. Pharmaceutically acceptable salts, include the acid addition salts (formed with the free amino groups of the protein) and which can be formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars or sodium chloride are included. Prolonged absorption of the injectable compositions can be brought about by the use in the compositions of agents delaying absorption, for example, aluminum monostearate and gelatin.

Sterile injectable solutions can be prepared by incorporating the active compounds in the required amount in the appropriate solvent with one or more of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of solvents, such as DMSO can be used to result in extremely rapid penetration, delivering high concentrations of the active agents to a small area.

Upon formulation, solutions can be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution can be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In particular embodiments, prolonged absorption of an injectable composition can be brought about by the use in the compositions of agents delaying absorption, such as, for example, aluminum monostearate, gelatin or combinations thereof.

In addition to the compounds formulated for parenteral administration, such as intravenous or intramuscular injection, other pharmaceutically acceptable forms include, e.g., liposomal formulations; and any other form currently used, including creams and topical formulations.

In certain embodiments, the use of liposomes and/or nanoparticles is contemplated for the formulation and administration of the therapeutic agents disclosed herein. The formation and use of liposomes is generally known to those of skill in the art.

Nanocapsules can generally entrap compounds in a stable and reproducible way. To avoid side effects due to intracellular polymeric overloading, such ultrafine particles (sized around 0.1 μm) can be designed using polymers able to be degraded in vivo. Biodegradable polyalkyl-cyanoacrylate nanoparticles that meet these requirements are contemplated for use in the present invention, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 Sonication of MLVs results in the formation of small unilamellar vesicles (SUVs) with diameters in the range of 200-500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is an example structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

The actual dosage amount of a composition of the present invention administered to a subject can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 5% to about 20%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, isotonic agents, such as, for example, sugars, sodium chloride or combinations thereof are included.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1-Anti-VLDL receptor monoclonal antibodies inhibit fibrin-VLDL receptor interaction and reduce fibrin-dependent inflammation in vivo In this example, two monoclonal antibodies whose epitopes overlap with the fibrin-binding site of VLDLR are identified. Furthermore, this example shows that these antibodies inhibit fibrin-VLDLR interaction and have an inhibitory effect on leukocyte transmigration in vitro. This example also demonstrates the anti-inflammatory properties and cardioprotective effect of these antibodies in in vivo models.

Among three previously generated anti-VLDLR mAbs, 1H5, 1H10, and 5F3, the epitopes for two of them have been previously partially characterized (Ruiz J, et al., J Lipid Res 2005; 46: 1721-1731). Namely, it was shown that mAb 1H5 and 1H10 both recognize recombinant VLDLR fragments containing CR-domains 1-8, 3-6, and 5-8, while mAb 1H10 failed to recognize a fragment containing CR-domains 1-4 and mAb 1H5 showed reduced binding to this fragment (Ruiz J, et al., J Lipid Res 2005; 46: 1721-1731). Based on these findings it was concluded that both antibodies prefer domains located within the C-terminal region of the VLDLR ligand binding region which includes domains 1-8 (Ruiz J, et al., J Lipid Res 2005; 46: 1721-1731). In the present example, binding of mAb 1H10 and 1H5 to CR-domains 1-8, 3-6, and 5-8 was confirmed; however, a very strong binding of both mAbs to CR-domains 1-4 (FIG. 1A) was also observed. Such a discrepancy may be connected with different methods of detection of the binding or the restricted number of VLDLR fragment used in the previous study. Whatever the reason for the discrepancy is, the binding experiments with smaller VLDLR fragments provided in this example disclosed herein allowed for more precise localization of the epitopes for mAb 1H10 and 1H5 and localization of the epitope for mAb 5F3.

The present example localized the epitope for mAb 1H10 to CR-domains 3-6. In contrast, the epitope for mAb 1H5 was localized herein to CR-domains 1-2 and 5-6, although the first CR-domain may not be part of the epitope as mentioned herein. The fact that these two pairs of CR-domains are not contiguous, may suggest that they are closely spaced in the 3D structure. Alternatively, mAb 1H5 may recognize identical sequences in these highly homologous CR-domains. Since among domains containing the epitope for mAb 1H10 and 1H5 (FIG. 1, panel B), domains 2-4 were shown to be involved in fibrin binding (Yakovlev S, Medved L., Biochemistry 2015; 54: 4751-4761), it was expected that both mAbs should inhibit the interaction of fibrin with VLDLR. This was directly confirmed by the data provided herein.

Figure 4:
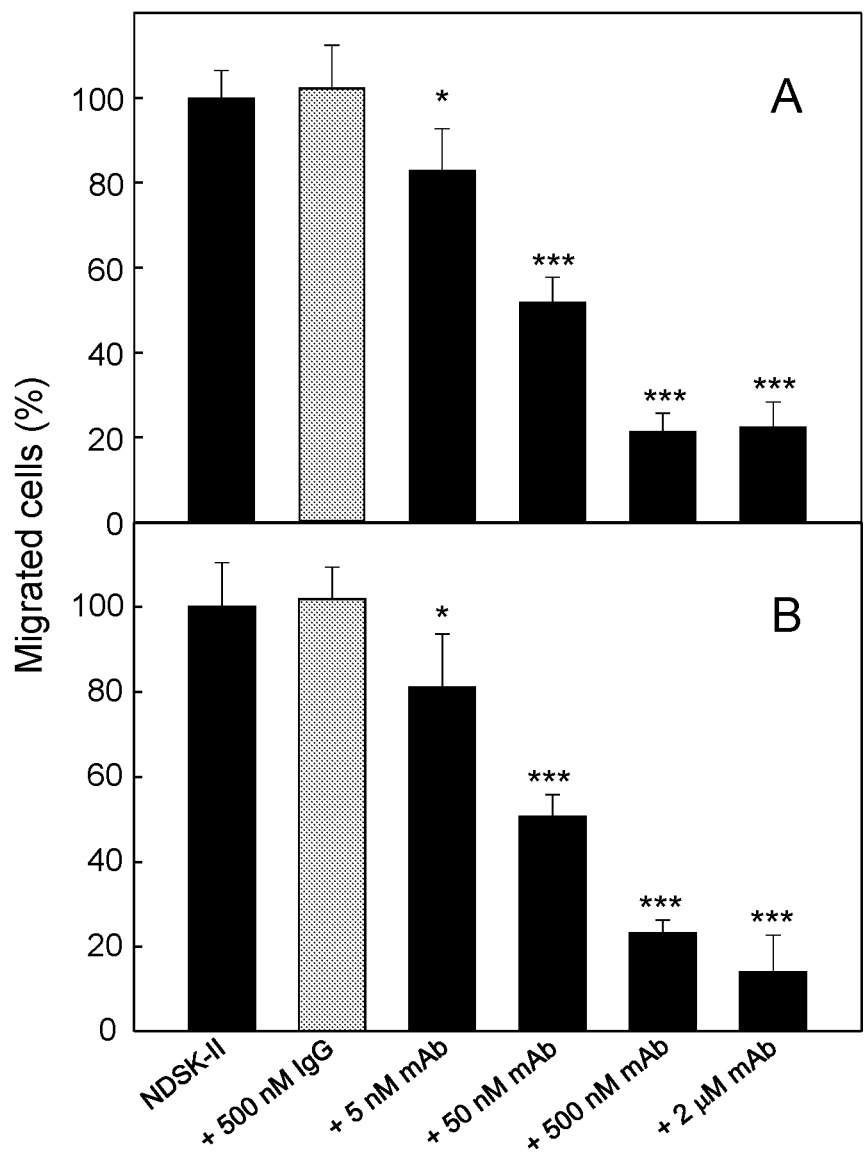
FIG. 4. Inhibitory effect of the anti-VLDLR monoclonal antibodies on NDSK-II-induced transendothelial migration of leukocytes (neutrophils) in vitro. HUVECs were cultured in medium containing 10% FBS for 48 hours before transmigration assays and then were grown to confluency on gelatin-coated cell culture inserts. Calcein AM-labeled HL-60 cells differentiated into neutrophil-like cells were added to the upper chambers on top of the HUVEC monolayers in the presence of 1.5 μM NDSK-II with or without IgG1κ or with increasing concentrations (from 5 nM to 2 μM) of mAb 1H10 (A) or mAb 1H5 (B). Mouse polyclonal antibodies IgGlκ were used as a negative IgG isotype control. The cells that migrated into the lower chambers were collected and quantified as described in Materials and methods. The number of cells that migrated in the absence of NDSK-II (control) were subtracted and the results were expressed as percentage of the cells that migrated in the presence of NDSK-II. Each graph shows combined data obtained from 2 independent experiments performed in triplicate; error bars denote means ±SD. *P<0.05; ***P<0.001.
Figure 5:
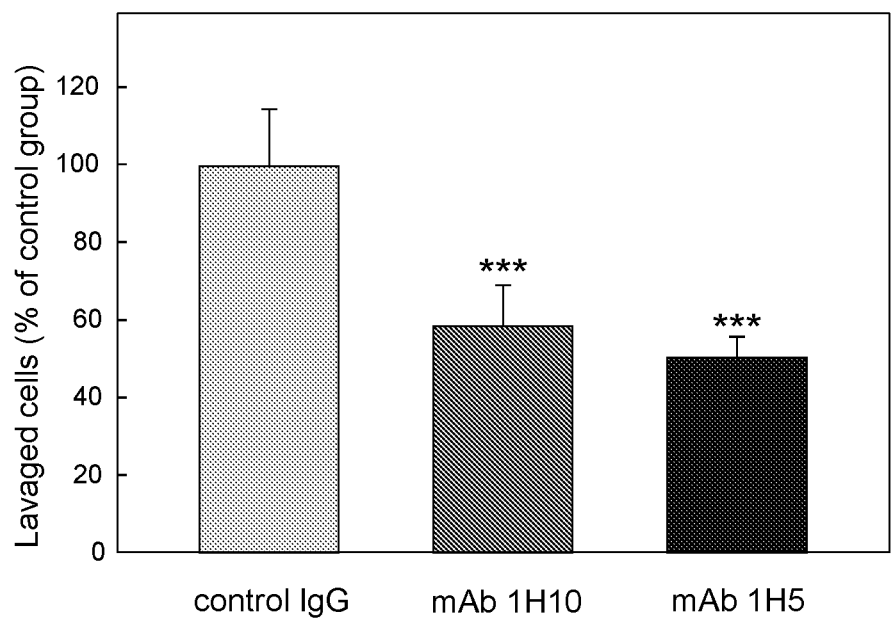
FIG. 5. Inhibitory effect of the monoclonal antibodies 1H10 and 1H5 on neutrophil infiltration in vivo in a mouse model of peritonitis. The monoclonal antibodies were injected intravenously, 100 μg mAb 1H10 or mAb 1H5 in 200 μL PBS in each mouse; control mice were injected with the same amount in the same volume of IgGκ. The number of infiltrated neutrophils was estimated as described in Materials and methods. The graph shows combined data from 2 independent experiments, and the results are means ±SD; ***P<0.001.
Figure 6:
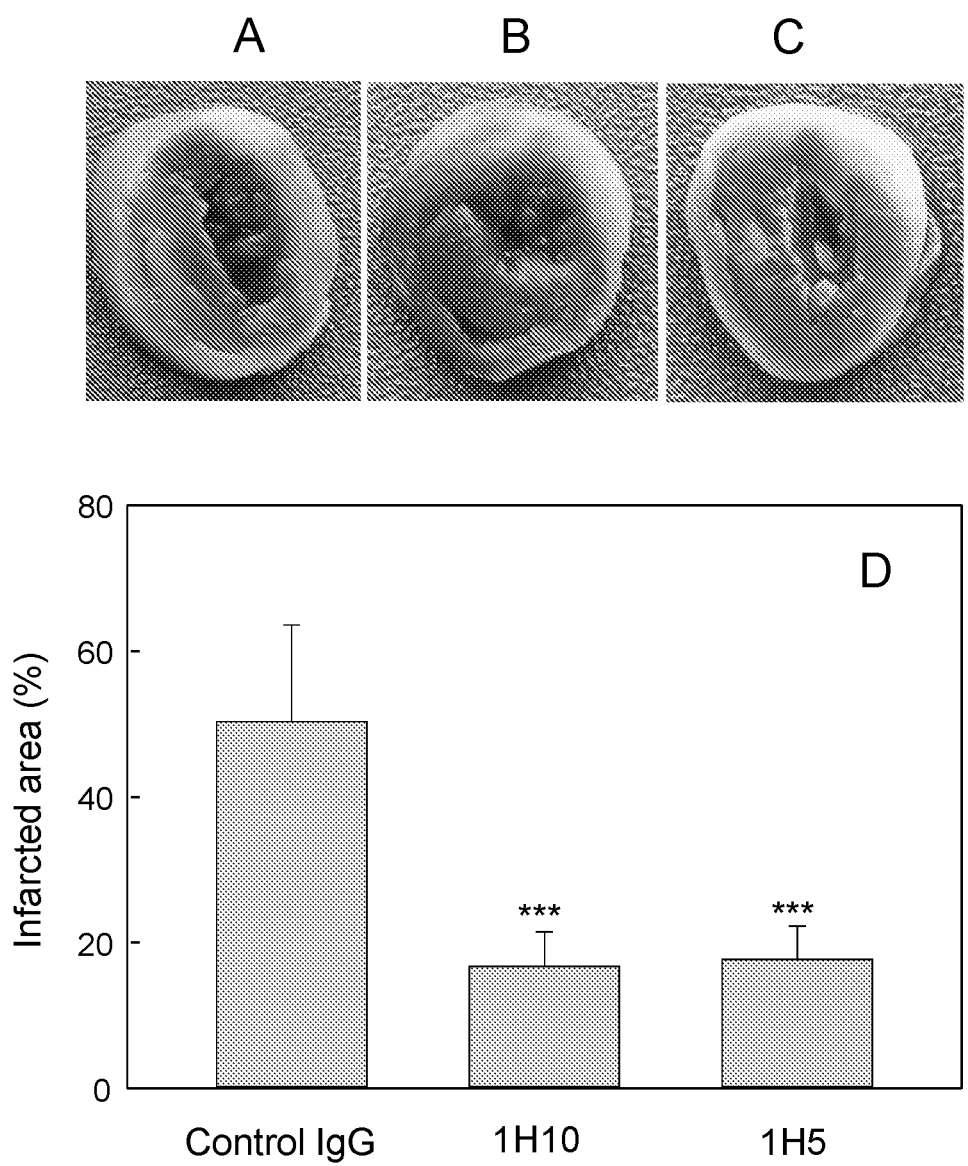
FIG. 6. Cardioprotective effect of mAb 1H10 and 1H5 during myocardial ischemia-reperfusion injury. Representative mouse heart slices after myocardial ischemia-reperfusion in mice treated with control IgGκ (A), mAb 1H10 (B), or mAb 1H5 (Panel C). The size of infarcted areas, which appear pale in color (A-C), was determined with ImageJ (NIH), and the results are present in (D) as a percentage of total area of the slices. The results are means ±SD (n=5). ***P<0.001.

This example reveals that mAb 1H10 and 1H5 both efficiently inhibit transendothelial migration of leukocytes. The inhibitory effect of these antibodies on the NDSK-II-induced leukocyte transmigration was very significant (-80%) (FIG. 4). The in vivo inhibitory effect of both mAbs on neutrophil infiltration into the peritoneum was less pronounced (~50%) but still significant (FIG. 5). Furthermore, the in vivo experiments of this example using mouse model of myocardial ischemia-reperfusion injury shows that treatment with either mAb 1H10 or 1H5 of mice subjected to ischemia-reperfusion reduced myocardial infarct size by more than two-fold (FIG. 6), indicating that these mAbs have significant cardioprotective effect. Thus, the present example shows that mAb 1H10 and 1H5 both are potent inhibitors of fibrin-VLDLR-dependent pathway of leukocyte transmigration and thereby inflammation.

In summary, the example provided herein has identified two anti-VLDLR monoclonal antibodies, mAb 1H10 and mAb 1H5, whose epitopes overlap with fibrin-binding domains of the VLDL receptor. Binding experiments revealed that both mAbs have high affinity to the fibrin-binding fragment of VLDLR and efficiently inhibit interaction of fibrin with this receptor. Furthermore, both mAbs efficiently inhibited transendothelial migration of leukocytes in the vitro experiments and significantly reduced infiltration of leukocytes in the peritoneum in the in vivo experiments. Finally, both antibodies exhibited significant cardioprotective effect in the experiments using mouse model of myocardial ischemia-reperfusion injury. Thus, monoclonal antibodies 1H10 and 1H5 are novel specific inhibitors of fibrin-VLDLR-dependent leukocyte transmigration pathway that may be developed as potent therapeutics for treatment of inflammation-related cardiovascular diseases including myocardial ischemia-reperfusion injury.

Material and Methods
Proteins, Antibodies, and Reagents

NDSK-II fragment was prepared by digestion of human fibrinogen (Enzyme Research Laboratories) with CNBr followed by cleavage of its fibrinopeptides with thrombin-agarose as described earlier (Bach T L, et al., J Biol Chem 1998; 273: 30719-30728; Yakovlev S, et al., J Thromb Haemost 2011; 9: 1847-1855). Human receptor-associated protein (RAP) was expressed in $E.$ $coli$ and purified as described (Williams S E, et al., J Biol Chem 1992; 267: 9035-9040). Anti-VLDLR monoclonal antibodies (mAb) 1H5, 1H10, and 5F3 (Ruiz J, et al., J Lipid Res 2005; 46: 1721-1731) were purified from hybridoma supernatants by affinity chromatography on Protein A-Sepharose (Sigma-Aldrich). Anti-VLDLR mAb E8 and 6A6 and anti-13-tubulin mAb G-8 were obtained from Santa Cruz Biotechnology. Purified mouse IgG1, κ isotype control antibody, was from Biolegend. Goat secondary anti-mouse antibodies conjugated with HRP and HRP substrate SureBlue TMB were from KPL. The anti-His(C-term) antibody (anti-His tag mAb) conjugated with HRP was from Invitrogen. Calcein AM fluorescent dye, phorbol 12-myristate 13-acetate (PMA), and N-formyl-Met-Leu-Phe (fMLP) were obtained from BD Biosciences, Promega, and Sigma-Aldrich, respectively.

Mice

C57BL/6J mice aged 8-12 weeks were from The Jackson Laboratory. All mice were housed in a pathogen-free facility, and all procedures were performed with approval of the University of Maryland Institutional Animal Care and Use Committee.

Preparation of Recombinant $(\beta15-66)_2$ and VLDLR Fragments

The recombinant $((\beta15-66)_2$ fragment was prepared as described earlier (Gorlatov S, Medved L., Biochemistry 2002; 41: 4107-4116; Yakovlev S, et al., J Thromb Haemost 2011; 9: 1847-1855). The soluble form of human VLDLR that contains its entire extracellular portion (sVLDLR) was prepared with the Drosophila Expression System as previously described (Ruiz J, et al., J Lipid Res 2005; 46: 1721-1731; Yakovlev S, Medved L., Biochemistry 2015; 54: 4751-4761). Recombinant fragments of VLDLR containing various combinations of its CR-domains, VLDLR(1-8), VLDLR(1-4), VLDLR(5-8), VLDLR(1-2), VLDLR(2-3), VLDLR(2-4), and VLDLR(3-4), were expressed in $E.$ $coli$, purified, and refolded as described earlier (Yakovlev S, Medved L., Biochemistry 2015; 54: 4751-4761). Two additional fragments, VLDLR(5-6) and VLDLR(7-8) containing CR-domains 5-6 and 7-8 (a.a. residues 164-248 and 249-328, respectively), both with His tag, were expressed in $E.$ $coli$ strain BL21(DE2)pLysS using a pET-20b expression vector. The cDNA fragments encoding these regions were produced by PCR using following primers in which the restrictase-recognition sequences are underlined:

5'-GATCGCCAACATATGCCAACCTGTGGCGCCCA-TG-3' (SEQ ID NO:12) (forward) and 5'-GCTGCT-CGAGTCAGTGGTGGTGGTGGTGGTGAGAGGGA-CAGTTGACCTCATC-3' (SEQ ID NO:13) (reverse) for VLDLR(5-6), and 5'-GATCGCCAACATATGCGAAC-TTGCCGACCTGAC-3' (SEQ ID NO:14) (forward) and 5'-GCTGCTCGAGTCAGTGGTGGTGGTGGTGGTGAC ACTCTTTCAGGGGCTCATC-3' (SEQ ID NO:15) (reverse) for VLDLR(7-8). The full-length cDNA encoding human VLDLR was used as a template. The PCR products were subcloned into the pET20b expression vector using NdeI and XhoI restriction sites and then transformed into DH5a *E. coli* host cells (Invitrogen). For preparation of VLDLR(5-6) and VLDLR(7-8), the BL21/pLysS *E. coli* host cells were transformed with the resulting plasmids and both fragments were produced, purified, and refolded following the procedures described earlier (Yakovlev S, Medved L., Biochemistry 2015; 54: 4751-4761). Concentrations of the newly expressed VLDLR fragments were determined spectrophotometrically using extinction coefficients (E280,1%) estimated from fragments' sequences by the ProtParam online tool (www.expasy.ch/tools/protparam-.html); their molecular masses were also estimated using this tool. The following molecular masses and $E_{280,1}\%$ values were obtained: VLDLR(5-6), 10.0 kDa and 11.7; VLDLR (7-8), 9.8 kDa and 6.4.

Solid-Phase Binding Assay

To map epitopes for the anti-VLDLR(1-8) mAb 1H10, 1H5, and 5F3, wells of Immulon 2HB microtiter plates were coated overnight at 4° C. with various VLDLR fragments, each at 1 µg/mL in 0.1M $Na_2CO_3$, pH 9.5 (coating buffer). The wells were then blocked with Blocker BSA in TBS (Thermo Scientific) for 1 hour at room temperature. Following washing with Tris-buffered saline (TBS) containing 0.05% Tween 20 and 1 mM $CaCl_2$ (binding buffer), the anti-VLDLR(1-8) mAbs, each at 1 µg/mL in the binding buffer, were added to the wells and incubated for 1 hour at 37° C. Bound mAbs were detected by reaction with the HRP-conjugated goat anti-mouse antibodies (1 hour at 37° C.). The peroxidase substrate, SureBlue TMB, was added to the wells, and the amount of bound mAbs was measured spectrophotometrically at 450 nm.

To estimate equilibrium dissociation constants ($K_d$), wells of Immulon 2HB microtiter plates were coated overnight at 4° C. with VLDLR(1-8) at 1 µg/mL in the coating buffer. The wells were blocked as above and the anti-VLDLR mAbs at indicated concentrations were added to the wells and incubated for 1 hour at 37° C. Bound mAbs were detected as described above. Data were analyzed by non-linear regression analysis using equation 1:

$$A = A_{max}/(1 + K_d/[L]) \quad (1)$$

where A represents the absorbance of the oxidized substrate, which is assumed to be proportional to the amount of mAb bound, Amax is the absorbance at saturation, [L] is the molar concentration of mAb, and $K_d$ is the equilibrium dissociation constant.

To test the inhibitory effect of mAb 1H10, 1H5, and 5F3, wells of Immulon 2HB microtiter plates were coated with $(\beta 15-66)_2$ at 2 µg/mL in the coating buffer overnight at 4° C. The wells were blocked as above, VLDLR(1-8) or sVLDLR at 10 nM in the binding buffer was pre-incubated with increasing concentrations of mAbs for 30 min at 37° C., and 100 µL aliquots of the mixture were added to the wells and incubated for 1 hour at 37° C. Bound VLDLR(1-8) or sVLDLR was detected by the reaction with the anti-His tag mAb as previously described (Yakovlev S, Medved L., Biochemistry 2015; 54: 4751-4761).

Cell Culture and Treatments

HUVECs (Lonza, Cat. #C2519AS) were cultured in EBM-2 basal medium supplemented with EGM SingleQuot Kit (Lonza), which contained 2% FBS, according to the manufacturer's instruction. HUVECs were also cultured in the same medium with 10% FBS. The HL-60 human promyelocytic cell line (ATCC) was cultured and differentiated to a neutrophil-like lineage as described earlier (Yakovlev S, et al., J Thromb Haemost 2011; 9: 1847-1855; Collins S J, et al., Proc Natl Acad Sci USA 1978; 75: 2458-2462). All cell cultures were maintained at 37° C. in 5% $CO_2$.

Leukocyte Transendothelial Migration Assay

Transendothelial migration experiments were performed with 24-well plates containing 8-µm pore size PET membrane inserts (BD Biosciences) as described earlier (Yakovlev S, et al., Blood 2012; 119: 637-644; Yakovlev S, et al., J Thromb Haemost 2011; 9: 1847-1855). Briefly, HUVECs were grown to confluence on the insert membrane and serum-starved for 2 hours before experiments. Calcein AM-labeled differentiated HL-60 cells were stimulated with PMA. Stimulated HL-60 cells in IMDM containing 1.5 µM NDSK-II without or with increasing concentrations of mAbs or 500 nM IgG1 (control) were added on top of the HUVEC monolayer. The inserts were placed into the wells containing chemoattractant fMLP, transmigration proceeded for 4 hours, and HL-60 cells migrated to the bottom wells were quantified with fluorescence plate reader.

Mouse Model of Peritonitis

Mice (6-8 per group) were injected intraperitoneally with 3.85% Bacto Fluid thioglycollate (1 mL per mouse) to induce leukocyte infiltration into the peritoneum. To test the effect of mAbs on leukocyte infiltration, mice received an intravenous injection (via the tail vein) of 100 µg mAb 1H10 or 1H5, both in 200 µL Phosphate Buffered Saline (PBS), prior to i.p. injections of thioglycollate. Mice in control groups received an intravenous injection of the same volume and amount of IgG1 in PBS. Four hours after the injections, each group of mice was euthanized, injected intraperitoneally with 3 mL ice-cold PBS, and total lavage fluid was withdrawn abdomens. Total cell number in lavage fluid was determined using a hemocytometer and the percentage of neutrophils (~90%) was determined by cytospin, as previously described (Cao C, et al., Blood 2005; 106: 3234-3241).

Mouse Model of Myocardial Ischemia-Reperfusion Injury

C57BL/6J mice were anesthetized initially with 4.5% Isoflurane and then maintained via face mask at 2% Isoflurane. An ocular lubricant paralube was applied to the animal eyes to prevent corneal desiccation. A 1 cm incision on the ventral surface of the neck over the trachea was made to expose trachea for visualization during orotracheal intubation with a 20G catheter (0.9-mm outside diameter). Mouse was connected to Harvard Rodent Ventilator, which is supplied with room air supplemented with oxygen at a rate of 105 breaths/min and with a tidal volume of 10-15 mL/kg body weight. The left jugular vein was isolated and ligated with 6-0 silk suture. A saline filled PE 10 tube was cannulated into the vein, and positioned to the superior vena cava. A midline thoracotomy was then made between the $3^{rd}$ and $4^{th}$ rib. The left coronary artery near the atrial appendage was ligated with an 8-0 silk suture and ischemia was maintained for 30 min after which the suture was removed to initiate blood flow into the ischemic myocardium. Each mAb or IgG1 (control), all at 320 µM in 50 µL PBS, was bolus injected via the jugular vein catheter into the mice twice, 1 min prior and 30 min after reperfusion. After 2-hours reperfusion, mice were euthanized and the hearts were retrieved. To identify infarcted areas, the hearts were perfused with 1% triphenyltetrazolium, cut into 2 mm-thick sections using a standard heart Matrix (Roboz), and the size of infarcted areas, which appears in pale color, was estimated using ImageJ program (NIH).

Statistical Analysis

Statistical analysis was done using Student's t-test with a P value of less than 0.05 being considered significant. All statistical analyses were performed in SigmaPlot 13.0 software (Systat Software).

Results

Epitope Mapping

To localize epitopes for the anti-VLDLR monoclonal antibodies, 1H5, 1H10, and 5F3, prepared earlier by immunizing VLDLR-deficient mice with the VLDLR(1-8) fragment containing eight CR-domains of VLDLR (Ruiz J, et al., J Lipid Res 2005; 46: 1721-1731), a number of previously described recombinant VLDLR fragments including CR-domains 1-4,5-8,1-2,2-3,3-4,2-4 were used (Yakovlev S, Medved L., Biochemistry 2015; 54: 4751-4761). In addition, two new fragments, VLDLR(5-6) and VLDLR(7-8), containing CR-domains 5-6 and 7-8 that were also prepared and used for epitope mapping.

Figure 2:
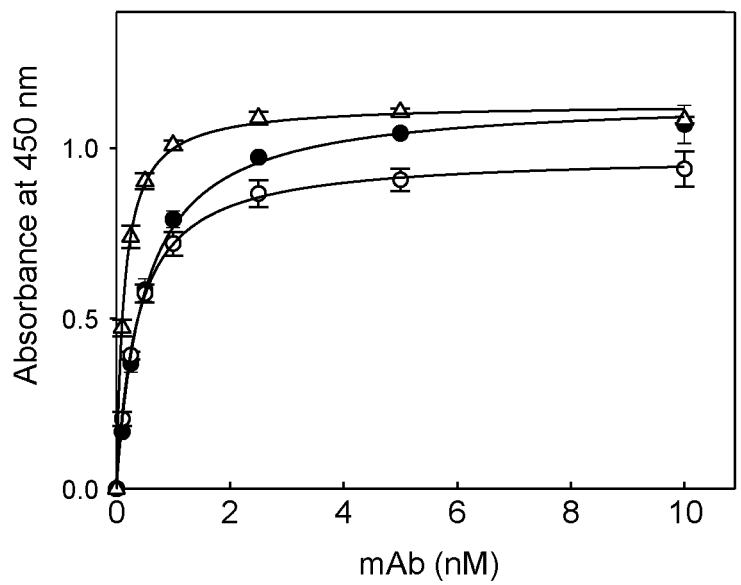
FIG. 2. ELISA-detected interaction between the anti-VLDLR monoclonal antibodies and the ligand-binding fragment of VLDLR. Increasing concentrations of the anti-VLDLR monoclonal antibodies 1H10 (filled circles), 1H5 (empty circles), and 5F3 (empty triangles) were incubated with microtiter wells coated with recombinant VLDLR (1-8) fragment, and the bound antibodies were detected with goat anti-mouse secondary antibodies as described in Materials and methods. The data are representative of 3 independent experiments; error bars represent the standard deviation of triplicate determinations. Solid lines represent best fits of the data.

In ELISA, when the three mAbs were incubated with all above mentioned VLDLR fragments, mAb 5F3 bound to VLDLR(1-8), VLDLR(5-8), and VLDLR(7-8); no reasonable binding was observed with the other fragments (FIG. 1A). These results indicate that the epitope for mAb 5F3 is located in CR-domains 7-8. In contrast, mAb 1H10 did not interact with VLDLR(7-8) while its interaction with the remaining fragments except VLDLR(1-2) was obvious, indicating that the epitope for this antibody is located in CR-domains 3-6. The third monoclonal antibody, 1H5, interacted with all fragments except VLDLR(3-4) and VLDLR(7-8), indicating that the epitope for this mAb is located in CR-domains 1-2 and 5-6. However, the fact that mAb 1H5 bound equally well to both VLDLR(1-2) and VLDLR(2-3) suggests that the first CR-domain may not be involved in mAb-binding. Location of the epitopes for all three mAbs is presented in FIG. 1B. It should be noted that the affinity of these mAbs to VLDLR(1-8) was very high. The $K_d$ values for the interaction of mAb 1H10, 1H5, and 5F3 with the VLDLR(1-8) fragment determined by ELISA were found to be 0.49±0.11, 0.31±0.06, and 0.12±0.02 nM, respectively (FIG. 2).

Inhibitory effect of anti-VLDLR mAbs on the interaction of VLDLR with fibrin

The VLDLR-binding site to the (3N-domains of fibrin (Yakovlev S, et al., Blood 2012; 119: 637-644) and the complementary fibrin-binding site to the CR-domains 2-4 of VLDLR was previously localized (Yakovlev S, Medved L., Biochemistry 2015; 54: 4751-4761). Since the epitopes for mAb 1H10 and 1H5 include CR-domains 3-4 and 2, respectively, it was hypothesized that these two mAbs should inhibit interaction of the VLDL receptor with fibrin. To test this hypothesis, the effect of all three mAbs on the interaction of the VLDLR(1-8) fragment with the $(\beta15\text{-}66)_2$ fragment representing the VLDLR-binding ($\beta$N-domains of fibrin was examined.

Figure 3:
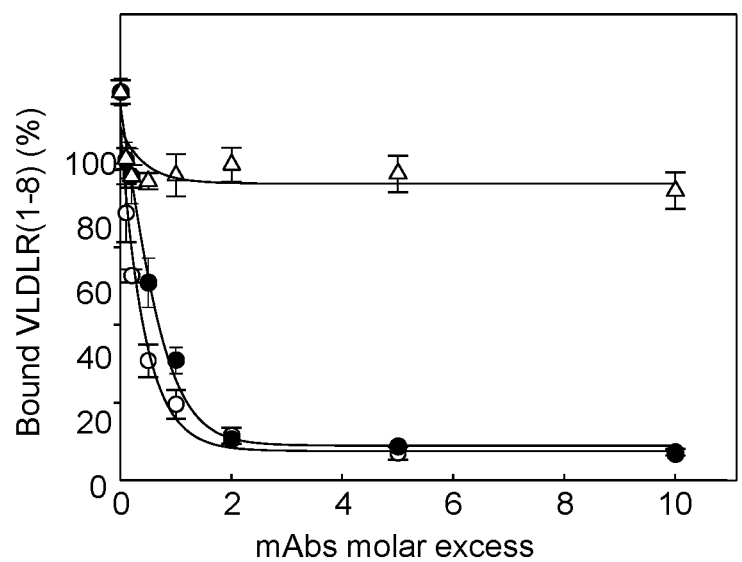
FIG. 3. Inhibitory effect of the anti-VLDLR monoclonal antibodies on the interaction between fibrin- and VLDLR-derived fragments detected by ELISA. Increasing concentrations of the anti-VLDLR monoclonal antibodies 1H10 (filled circles), 1H5 (empty circles), and 5F3 (empty triangles) were preincubated with the VLDLR (1-8) fragment, the mixtures were added to microtiter wells coated with the fibrin $(1315-66)_2$ fragment, and the bound VLDLR(1-8) was detected with the anti-His tag monoclonal antibody, as described in the Examples. The data are expressed as a percentage of control binding in the absence of the anti-VLDLR mAbs and are representative of 3 independent experiments; error bars represent the standard deviation of triplicate determinations.

In ELISA experiments, when VLDLR(1-8) was incubated with increasing concentrations of each of the three antibodies and then added to immobilized $(\beta15\text{-}66)_2$, mAb 1H10 and 1H5 both inhibited binding of VLDLR(1-8) to $(\beta15\text{-}66)_2$ in a concentration-dependent manner while mAb 1F5 exhibited very little effect (FIG. 3). The inhibition was practically complete at about 2-fold molar excess of mAb 1H10 and 1H5 over VLDLR(1-8). Similar results were obtained when sVLDLR representing the extracellular portion of the VLDLR receptor was used instead of VLDLR (1-8) (not shown). Since mAb 1H5 and 1H10 both efficiently inhibited interaction between the $(\beta15\text{-}66)_2$ fragment and VLDLR(1-8) or sVLDLR, it was hypothesized that these mAbs should also inhibit previously discovered fibrin-VLDLR-dependent transendothelial migration of leukocytes (Yakovlev S, et al., Blood 2012; 119: 637-644) and thereby inflammation. To test this hypothesis, the following experiments were performed.

Inhibitory Effect of the mAb 1H10 and 1H5 on Leukocyte Transmigration in vitro

To study the effect of mAb 1H10 and 1H5 on leukocyte transmigration in vitro, a leukocyte transendothelial migration assay was used. For this assay, HL-60 cells were differentiated into neutrophil-like cells using a procedure described by Hauert et al. (Hauert AB, et al., Int J Biochem Cell Biol 2002; 34: 838-854), who demonstrated that such cells constitute a valid model system for the analysis of human neutrophil migration. Transmigration of the differentiated cells across a confluent HUVEC monolayer was stimulated by fibrin mimetic NDSK-II, which was shown to be a potent stimulator of leukocyte transmigration (Petzelbauer P, et al., Nat Med 2005; 11: 298-304; Yakovlev S, et al., Blood 2012; 119: 637-644; Yakovlev S, et al., J Thromb Haemost 2011; 9: 1847-1855).

FIG. 4, Panel A shows the results of transmigration experiments indicating that control IgG1 had no effect on NDSK-II-induced leukocyte transmigration while mAb 1H10 inhibited this process in a concentration-dependent manner with the saturation at about 500 nM. The inhibitory effect of mAb 1H10 at this and higher concentrations was found to be about 80% indicating that in this in vitro model NDSK-II-induced leukocyte transmigration is carried out mainly through the fibrin-VLDLR-dependent pathway. The results obtained with mAb 1H5 were very similar (FIG. 4, panel B). Thus, mAb 1H10 and 1H5 both efficiently inhibited transendothelial migration of leukocytes in these in vitro experiments.

In vivo Study of the Anti-Inflammatory Effect of mAb 1H10 and 1H5

To test the effect of mAb 1H10 and 1H5 on leukocyte transmigration in vivo, a mouse model of peritonitis was used in which leukocyte migration from the circulation into the peritoneum is stimulated by intraperitoneal injection of thioglycollate, and leukocyte (neutrophil) accumulation is evaluated after 4 hours by counting the cells in the peritoneal lavage. In the experiments herein, each mouse was injected intravenously with mAb 1H10 or mAb 1H5 prior to intraperitoneal injection of thioglycollate; control mice received an intravenous injection of non-specific IgG1. The experiments revealed that the number of neutrophils accumulating in the peritoneum of mAb-treated mice was about 2-fold lower than that in the control mice (FIG. 5). This indicates that both monoclonal antibodies, 1H10 and 1H5, efficiently inhibited leukocyte transmigration and thereby inflammation in vivo.

Testing the Cardioprotective Effect of mAb 1H10 and 1H5

To evaluate the potential of the anti-VLDLR mAbs for myocardial infarction therapy, a mouse model of myocardial ischemia-reperfusion injury was used. In this model, ischemia is achieved by ligation of the left coronary artery with a suture; after 30 min the suture is cut to initiate blood flow into the ischemic myocardium (reperfusion) and the size of infarcted area is evaluated after 2 hours of reperfusion.

Using this model, the cardioprotective effect of both mAbs, 1H10 and 1H5 was tested. Each antibody was injected via the jugular vein into the mice twice, control mice were injected with non-specific IgG1. The results presented in FIG. 6 indicate that infarct size in mice treated with both mAbs was reduced by about two-fold in comparison with that in control mice. Thus, in this in vivo model both monoclonal antibodies, 1H10 and 1H5, exhibited significant cardioprotective effect.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

---

What is claimed is:

1. A method of treating a pathophysiological effect of ischemia and reperfusion, comprising administering to a subject in need thereof after the reperfusion a therapeutically effective amount of an antibody, wherein the antibody comprises complementarity determining regions (CDRs) of antibody 1H10, wherein the antibody inhibits binding of fibrin to Very Low Density Lipoprotein Receptor (VLDLR).

2. The method of claim 1, wherein the antibody binds at least one complement-type repeat (CR) domain of VLDLR selected from the group consisting of CR-2, CR-3 and CR-4.

3. The method of claim 1, wherein the administration inhibits transendothelial migration of leukocytes in the subject.

4. The method of claim 1, wherein the administration inhibits injury induced by ischemia and reperfusion in the subject.

5. The method of claim 1, wherein the administration inhibits myocardial injury induced by ischemia and reperfusion in the subject.

6. The method of claim 1, wherein the antibody is a monoclonal antibody.

7. The method of claim 6, wherein the antibody is humanized.

8. The method of claim 1, further comprising administering to the subject a therapeutically effective amount of a peptide comprising a fibrin beta chain fragment of the Bβ chain of fibrinogen.

9. The method of claim 8, wherein the peptide comprises an amino acid sequence of a fibrin beta chain fragment of a Bbeta chain of fibrinogen wherein said peptide comprises a non-naturally occurring amino acid residue and wherein said peptide does not comprise a sequence that is wild-type β15-42 monomer sequence and does not comprise (β15-66)$_2$ dimer sequence, wherein said dimer consists of identical monomers consisting of wild-type amino acids β15-65 and a non-naturally occurring Gly at position 66 of each chain.

10. The method of claim 9, wherein said peptide comprises a Cys and a Gly at successive amino acid residues.

11. The method of claim 8, wherein said peptide is in monomeric or dimeric form.

12. The method of claim 11, wherein said peptide is in dimeric form.

13. The method of claim 12, wherein said dimer comprises two identical peptides, each of said peptides comprising amino acids 15-30 of a fibrin beta chain or a VE-cadherin-binding conservative variant thereof, each of said peptides being linked at C-terminal ends thereof, and said dimer having fewer than 104 amino acid residues in total.

14. The method of claim 12, wherein said dimer is disulfide linked at a Cys residue in said peptide.

15. The method of claim 8, wherein the peptide comprises an amino acid sequence selected from the group consisting of any of SEQ ID NOS: 1-7.

16. The method of claim 8, wherein said peptide is conjugated to, fused with, or combined with a protein transduction domain (PTD).

17. The method of claim 1, wherein the antibody is 1H10.

18. The method of claim 8, wherein the peptide inhibits binding of fibrin to VE-cadherin.

19. The method of claim 1, wherein the ischemia and reperfusion is myocardial ischemia and reperfusion.

20. The method of claim 1, wherein the subject is suffering from or at risk of myocardial infarction or stroke.

21. The method of claim 1, wherein the ischemia and reperfusion is selected from the group consisting of hepatic ischemia and reperfusion, renal ischemia and reperfusion, intestinal ischemia and reperfusion, or other gastrointestinal ischemia and reperfusion, neuronal ischemia and reperfusion, ischemic neuropathies, surgical-induced ischemia and reperfusion, ischemia and reperfusion associated with organ transplantation and preservation of an ischemic and reperfused organ for organ transplantation.

22. The method of claim 1, wherein the subject is suspected of undergoing ischemia and reperfusion, susceptible of undergoing ischemia and reperfusion, or known to be undergoing ischemia and reperfusion.

23. The method of claim 1, wherein the subject is going under programmed or planned ischemia and reperfusion.

24. The method of claim 23, wherein the programmed or planned ischemia and reperfusion is cardiac bypass surgery, angioplasty, or other cardiovascular surgeries or procedures.

25. The method of claim 1, wherein the ischemia and reperfusion is an acute condition rather than a long-term or chronic condition.

* * * * *